United States Patent [19]

Bourgery et al.

[11] Patent Number: 4,831,051

[45] Date of Patent: May 16, 1989

[54] AROMATIC DERIVATIVES COMPRISING AN AMINOALKOXY CHAIN, THE SALTS THEREOF, THE PROCESS FOR PREPARING THESE DERIVATIVES AND SALTS AND THE APPLICATION THEREOF IN THERAPEUTICS

[75] Inventors: Guy R. Bourgery, Colombes; Alain P. Lacour, La Varenne; Bernard M. Pourrias, Meudon La Foret; Raphaël Santamaria, Paris, all of France

[73] Assignee: Delande S.A., France

[21] Appl. No.: 147,268

[22] Filed: Jan. 22, 1988

Related U.S. Application Data

[62] Division of Ser. No. 748,862, Jun. 26, 1985, Pat. No. 4,732,896, which is a division of Ser. No. 451,537, Dec. 21, 1982, Pat. No. 4,536,500.

[30] Foreign Application Priority Data

Dec. 24, 1981 [FR] France ................................. 81 24244
Dec. 15, 1982 [FR] France ................................. 82 21053

[51] Int. Cl.$^4$ .................. A61K 31/33; A61K 31/135; C07D 319/18; C07D 91/06
[52] U.S. Cl. ..................................... 514/452; 514/651; 549/362; 564/352; 564/353; 564/354
[58] Field of Search .................... 564/352, 353, 354; 549/362; 514/452, 651

[56] References Cited

U.S. PATENT DOCUMENTS 2,668,850 2/1954 Goldberg et al. ................... 564/354

OTHER PUBLICATIONS

Boissier, Jr. et al., Arzneimittelforsch, 19(9), 1193–6, (1967), (only the Index Chemicus Abstract is supplied).

*Primary Examiner*—Nicky Chan
*Attorney, Agent, or Firm*—Roylance, Abrams, Berdo & Goodman

[57] ABSTRACT

New aromatic derivatives having an activity antagonistic to calcium and corresponding to formula:

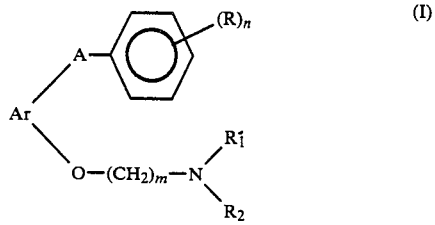

in which:

A represents a chain having any one of the following structures:

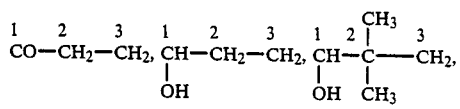

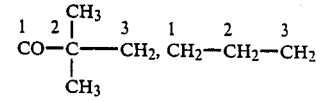

Ar represents a group of structure:

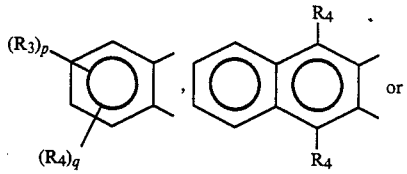

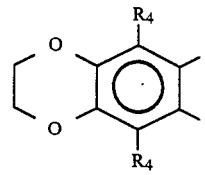

n takes the value 1 or 2 when R is different from H;
m takes the value 2 or 3.

6 Claims, No Drawings

AROMATIC DERIVATIVES COMPRISING AN AMINOALKOXY CHAIN, THE SALTS THEREOF, THE PROCESS FOR PREPARING THESE DERIVATIVES AND SALTS AND THE APPLICATION THEREOF IN THERAPEUTICS

This is a division of application Ser. No. 748,862 filed June 26, 1985, now U.S. Pat. No. 4,732,896, which was a division of application Ser. No. 451,537, filed Dec. 21, 1982 now U.S. Pat. No. 4,536,500.

The present invention relates to new aromatic derivatives comprising an aminoalkoxy chain, the salts thereof, the process for preparing these derivatives and salts and the application thereof in therapeutics.

More precisely, the new derivatives of the invention correspond to the general formula:

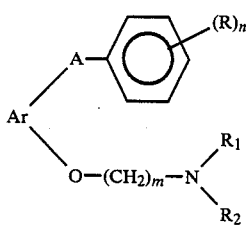     (I)

in which:
R represents a hydrogen or halogen atom, a methyl, hydroxyl or alkoxy group in which the alkyl residue comprises 1 to 4 carbon atoms, or a benzyloxy group;
n takes the value 1 or 2 when R is different from H;
m takes the value 2 or 3;
A represents a chain having any one of the following structures:

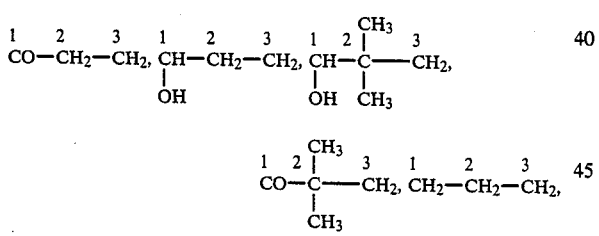

the aromatic group Ar being linked to position 1 of this chain,
the pair ($R_1$, $R_2$) takes the value (H, $C_1$-$C_4$ alkyl), (H, $C_5$-$C_6$ cycloalkyl) or (H, cycloalkylalkyl comprising from 4 to 8 carbon atoms, except in the case where A=

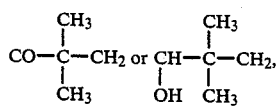

or else the value ($C_1$-$C_4$ alkyl, $C_1$-$C_4$ alkyl), $R_1$ and $R_2$ being also able to form in conjunction with the nitrogen atom to which they are linked a radical chosen from the following: pyrrolidino, piperidino, hexamethyleneimino, morpholino; and
Ar represents:
either a benzene group of structure:

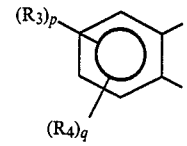

in which $R_3$ represents a halogen atom or a nitro or methyl group, $R_4$=alkoxy with 1 to 4 carbon atoms, p=0, 1 or 2; q=0, 1, 2, 3, 4; p+q≦4 with the restrictions, when A=CO—$CH_2$—$CH_2$ or

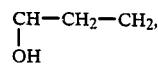

that p and q cannot simultaneously take the value 0 or a naphthalene or benzodioxannic group respectively of structure:

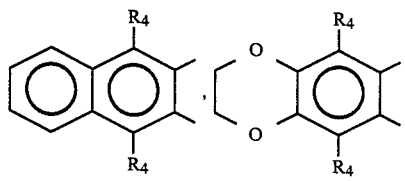

where $R_4$ has the same meanings as previously.

The salts of the derivatives of formula (I) are formed by the acid addition salts of said derivatives of formula (I), the acid being a mineral acid such as hydrochloric acid or an organic acid such as oxalic acid.

The present invention further relates to the process for preparing these derivatives and salts. More precisely:

(A) The derivatives (I) for which A represents the chain of structure CO—$CH_2$—$CH_2$ are obtained:
either by reduction by catalytic hydrogenation more especially with Raney's nickel, preferably in a hydro-alcohol medium, respectively of the compounds of formula:

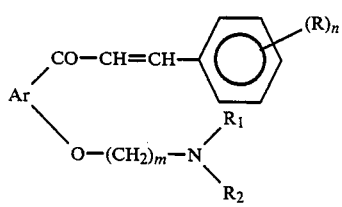     (II)

in which R, n, m, $R_1$, $R_2$ and Ar have the same meanings as in formula (I),
or, when R represents a hydroxyl group, by simultaneous reduction and debenzylation, more particularly with palladium on charcoal, preferably in a hydro-alcohol medium and in the presence of hydrochloric acid, respectively of the corresponding compounds of formula (II) and for which R represents a benzyloxy group.

(B) The derivatives of formula (I) for which R represents the chain of structure $$\underset{\mathrm{OH}}{\mathrm{CH}}-\mathrm{CH_2-CH_2,}$$

are obtained:

(a) by respective reduction of the corresponding compounds of formula (I) preferably with the sodium borohydride-pyridine complex, more particularly in an alcohol medium and in the presence of NaOH, preferably concentrated, this latter being in a quantity at least stoechiometric when R in formula (II) represents a hydroxyl group and in an amount at least twice stoechiometric when $(R)_n$ represents two hydroxyl groups;

(b) by reduction preferably with the sodium borohydride alone, more particularly in an alcohol medium, respectively of the corresponding compounds of formula (I) for which A represents the chain of structure CO—CH$_2$—CH$_2$ and whose preparation is described in paragraph (A) above;

(c) when in formula (I) R represents a hydroxyl group, by hydrogenolysis more particularly with palladium on charcoal, preferably in a hydro-alcohol medium, possibly in the presence of hydrochloric acid, respectively of the corresponding compounds of formula (I) in which A=

$$\underset{\mathrm{OH}}{\mathrm{CH}}-\mathrm{CH_2-CH_2}$$

and R represents the benzyloxy group; or (d) when in formula (I) R has the same meanings as before, except the value OH, by reduction, by means of an excess of sodium borohydride, of the compounds of formula (II) except for those in which R=OH.

(C) The compounds of formula (I) in which R represents the chain of structure CH$_2$—CH$_2$—CH$_2$ are obtained by reduction preferably with triethylsilane in the presence of trifluoroacetic acid respectively of the corresponding compounds of formula (I) for which A=—CO—CH$_2$—CH$_2$ and whose preparation is described in paragraph (A) above.

(D) The compounds of formula (I) for which A represents the chain of structure $$\mathrm{CO-\underset{\underset{CH_3}{|}}{\overset{\overset{CH_3}{|}}{C}}-CH_2}$$

and R has the same meanings as in formula (I) without however being able to represent a hydroxyl group, are obtained by condensation, preferably in a tetrahydrofurannic medium, in the presence of sodium hydride, of the compounds of formula:

$$\mathrm{Ar}\diagdown\!\!\!\!\overset{\mathrm{CO}-\!\!\!\diagup}{\underset{\mathrm{O-(CH_2)}_m-\mathrm{N}\diagdown\!\!\!\overset{R'_1}{\underset{R'_2}{}}}{}} \qquad\text{(III)}$$

in which Ar and m have the same meanings as in formula (I) and the pair (R'$_1$, R'$_2$)=(C$_1$–C$_4$ alkyl, C$_1$–C$_4$ alkyl) or R'$_1$ and R'$_2$ form in conjunction with the nitrogen atom to which they are linked, a pyrrolidino, piperidino, hexamethyleneimino or morpholino radical, respectively with the compounds of formula:

$$\mathrm{X-CH_2-}\!\!\!\overset{(R')_n}{\bigcirc} \qquad\text{(IV)}$$

in which X represents a good leaving group such as a halogen atom or a mesyloxy or tosyloxy group and R' has the same meanings as R in formula (I) without however being able to represent a hydroxyl group.

(E) The compounds of formula (I) for which R represents the chain of structure $$\mathrm{CO-\underset{\underset{CH_3}{|}}{\overset{\overset{CH_3}{|}}{C}}-CH_2}$$

and R represents the hydroxyl radical are obtained by catalytic debenzylation (or hydrogenolysis), more particularly in the presence of palladium on charcoal and in an alcohol medium, possibly in the presence of hydrochloric acid, respectively of the corresponding compounds of formula (I) for which A=

$$\mathrm{CO-\underset{\underset{CH_3}{|}}{\overset{\overset{CH_3}{|}}{C}}-CH_2}$$

and R represents the benzyloxy group prepared according to paragraph (D) above.

(F) The compounds of formula (I) for which A represents the chain of structure $$\mathrm{\underset{\phantom{|}}{\overset{OH}{|}}\underset{\underset{CH_3}{|}}{\overset{\overset{CH_3}{|}}{C}}-CH_2}\atop\mathrm{CH-C-CH_2}$$

are obtained by reduction, more particularly by means of sodium borohydride preferably in an alcohol medium, respectively of the corresponding compounds of formula (I) for which A=

$$\mathrm{CO-\underset{\underset{CH_3}{|}}{\overset{\overset{CH_3}{|}}{C}}-CH_2}$$

and prepared according to paragraphs (D) and (E) above.

The compounds of formula (II) are obtained by condensation of the compounds of formula:

$$\mathrm{Ar}\diagdown\!\!\!\!\overset{\mathrm{COCH_3}}{\underset{\mathrm{O-(CH_2)}_m-\mathrm{N}\diagdown\!\!\!\overset{R_1}{\underset{R_2}{}}}{}} \qquad\text{(V)}$$

in which m, —NR$_1$R$_2$ and Ar have the same meanings as in formula (II), respectively with the aromatic aldehydes of formula

AROMATIC DERIVATIVES COMPRISING AN AMINOALKOXY CHAIN, THE SALTS THEREOF, THE PROCESS FOR PREPARING THESE DERIVATIVES AND SALTS AND THE APPLICATION THEREOF IN THERAPEUTICS

This is a division of application Ser. No. 748,862 filed June 26, 1985, now U.S. Pat. No. 4,732,896, which was a division of application Ser. No. 451,537, filed Dec. 21, 1982 now U.S. Pat. No. 4,536,500.

The present invention relates to new aromatic derivatives comprising an aminoalkoxy chain, the salts thereof, the process for preparing these derivatives and salts and the application thereof in therapeutics.

More precisely, the new derivatives of the invention correspond to the general formula:

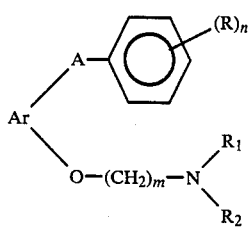
(I)

in which:

R represents a hydrogen or halogen atom, a methyl, hydroxyl or alkoxy group in which the alkyl residue comprises 1 to 4 carbon atoms, or a benzyloxy group; n takes the value 1 or 2 when R is different from H; m takes the value 2 or 3;

A represents a chain having any one of the following structures:

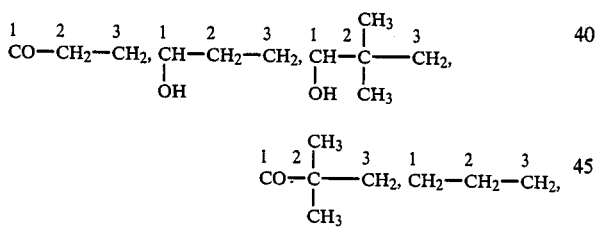

the aromatic group Ar being linked to position 1 of this chain, the pair ($R_1$, $R_2$) takes the value (H, $C_1$-$C_4$ alkyl), (H, $C_5$-$C_6$ cycloalkyl) or (H, cycloalkylalkyl comprising from 4 to 8 carbon atoms, except in the case where A=

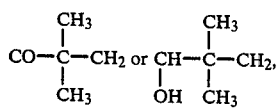

or else the value ($C_1$-$C_4$ alkyl, $C_1$-$C_4$ alkyl), $R_1$ and $R_2$ being also able to form in conjunction with the nitrogen atom to which they are linked a radical chosen from the following: pyrrolidino, piperidino, hexamethyleneimino, morpholino; and Ar represents:

either a benzene group of structure:

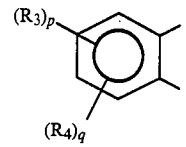

in which $R_3$ represents a halogen atom or a nitro or methyl group, $R_4$=alkoxy with 1 to 4 carbon atoms, p=0, 1 or 2; q=0, 1, 2, 3, 4; p+q≦4 with the restrictions, when A=CO—$CH_2$—$CH_2$ or

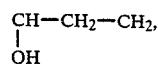

that p and q cannot simultaneously take the value 0 or a naphthalene or benzodioxannic group respectively of structure:

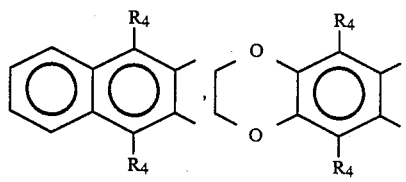

where $R_4$ has the same meanings as previously.

The salts of the derivatives of formula (I) are formed by the acid addition salts of said derivatives of formula (I), the acid being a mineral acid such as hydrochloric acid or an organic acid such as oxalic acid.

The present invention further relates to the process for preparing these derivatives and salts. More precisely:

(A) The derivatives (I) for which A represents the chain of structure CO—$CH_2$—$CH_2$ are obtained:

either by reduction by catalytic hydrogenation more especially with Raney's nickel, preferably in a hydro-alcohol medium, respectively of the compounds of formula:

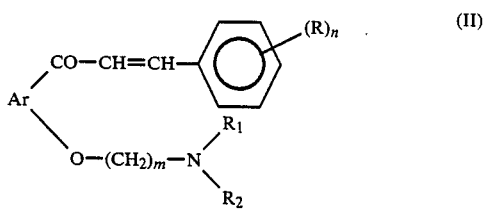
(II)

in which R, n, m, $R_1$, $R_2$ and Ar have the same meanings as in formula (I), or, when R represents a hydroxyl group, by simultaneous reduction and debenzylation, more particularly with palladium on charcoal, preferably in a hydro-alcohol medium and in the presence of hydrochloric acid, respectively of the corresponding compounds of formula (II) and for which R represents a benzyloxy group.

(B) The derivatives of formula (I) for which R represents the chain of structure

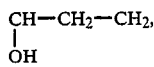

are obtained:

(a) by respective reduction of the corresponding compounds of formula (I) preferably with the sodium borohydride-pyridine complex, more particularly in an alcohol medium and in the presence of NaOH, preferably concentrated, this latter being in a quantity at least stoechiometric when R in formula (II) represents a hydroxyl group and in an amount at least twice stoechiometric when $(R)_n$ represents two hydroxyl groups;

(b) by reduction preferably with the sodium borohydride alone, more particularly in an alcohol medium, respectively of the corresponding compounds of formula (I) for which A represents the chain of structure $CO-CH_2-CH_2$ and whose preparation is described in paragraph (A) above;

(c) when in formula (I) R represents a hydroxyl group, by hydrogenolysis more particularly with palladium on charcoal, preferably in a hydro-alcohol medium, possibly in the presence of hydrochloric acid, respectively of the corresponding compounds of formula (I) in which A=

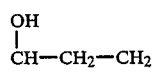

and R represents the benzyloxy group; or (d) when in formula (I) R has the same meanings as before, except the value OH, by reduction, by means of an excess of sodium borohydride, of the compounds of formula (II) except for those in which R=OH.

(C) The compounds of formula (I) in which R represents the chain of structure $CH_2-CH_2-CH_2$ are obtained by reduction preferably with triethylsilane in the presence of trifluoroacetic acid respectively of the corresponding compounds of formula (I) for which A=- $CO-CH_2-CH_2$ and whose preparation is described in paragraph (A) above.

(D) The compounds of formula (I) for which A represents the chain of structure

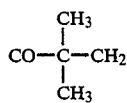

and R has the same meanings as in formula (I) without however being able to represent a hydroxyl group, are obtained by condensation, preferably in a tetrahydrofurannic medium, in the presence of sodium hydride, of the compounds of formula:

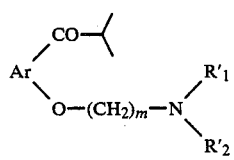

in which Ar and m have the same meanings as in formula (I) and the pair $(R'_1, R'_2)=(C_1-C_4$ alkyl, $C_1-C_4$ alkyl) or $R'_1$ and $R'_2$ form in conjunction with the nitrogen atom to which they are linked, a pyrrolidino, piperidino, hexamethyleneimino or morpholino radical, respectively with the compounds of formula:

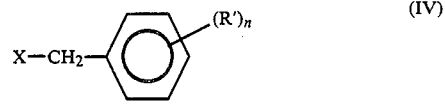

in which X represents a good leaving group such as a halogen atom or a mesyloxy or tosyloxy group and R' has the same meanings as R in formula (I) without however being able to represent a hydroxyl group.

(E) The compounds of formula (I) for which R represents the chain of structure

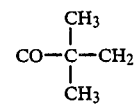

and R represents the hydroxyl radical are obtained by catalytic debenzylation (or hydrogenolysis), more particularly in the presence of palladium on charcoal and in an alcohol medium, possibly in the presence of hydrochloric acid, respectively of the corresponding compounds of formula (I) for which A=

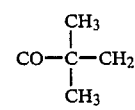

and R represents the benzyloxy group prepared according to paragraph (D) above.

(F) The compounds of formula (I) for which A represents the chain of structure

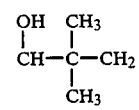

are obtained by reduction, more particularly by means of sodium borohydride preferably in an alcohol medium, respectively of the corresponding compounds of formula (I) for which A=

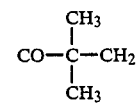

and prepared according to paragraphs (D) and (E) above.

The compounds of formula (II) are obtained by condensation of the compounds of formula:

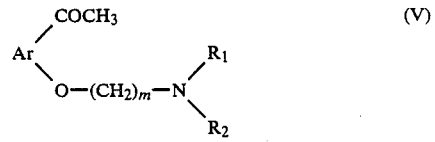

in which m, $-NR_1R_2$ and Ar have the same meanings as in formula (II), respectively with the aromatic aldehydes of formula in which $R_5$ has the same meanings as in formula (XVII) and which consists (a) in treating said compounds of formula (XVIII) with 36% hydrogen peroxid in the presence of formic acid (so-called BAYER-WIL-LIGER reaction), then (b) in treating the compounds obtained with aluminium chloride in the presence of an acid chloride of formula $R_5COCl$ where $R_5$ has the same meanings as in formula (XVII), in solution in methylene chloride (so-called FRIES reaction), then (c) in treating the compounds obtained with an alkyl halide or an alkyl sulfate of formula $R_4Br$, $R_4Cl$ or $(R_4)_2SO_4$ where $R_4$ has the same meaning as in formula (XVII), in the presence of potassium carbonate, in an aprotic solvent (such as acetone for example), then (d) in treating the compounds obtained with potassium carbonate in an alcohol medium (preferably methanol) and finally (e) in treating the compounds obtained with an alkyl halide or an alkyl sulfate of formula $R_4Br$, $R_4Cl$ or $(R_4)_2SO_4$ where $R_4$ has the same meaning as above in the presence of potassium carbonate, in an aprotic solvent (such as acetone for example).

The compounds of formula (VIII) having the particular structure:

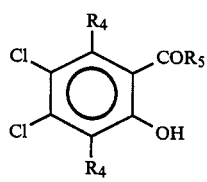

(VIIIe)

in which $R_4$ has the same meanings as in formula (I) and $R_5$ has the same meanings as in formula (VIII) are obtained by action of chlorine in a chloroform medium, at 20° C., on the compounds of formula:

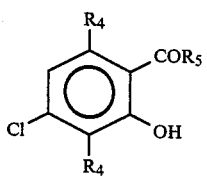

(VIIIn)

where $R_4$ and $R_5$ have the same meanings as in formula (VIIIe), the compounds of formula (VIIIn) being obtained by catalytic debenzylation ($H_2$, Pd/C, EtOH) of the corresponding compounds of formula (XII).

The compounds of formula (VIII) having the particular structure:

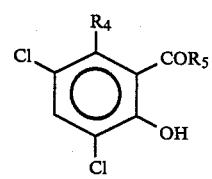

(VIIIf)

in which $R_4$ and $R_5$ have the same meanings as in formula (VIIIe) are obtained by action of chlorine in a chloroform medium at 20° C. on the compounds of formula (VIII) having the particular structure:

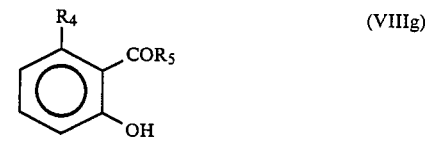

(VIIIg)

in which $R_4$ and $R_5$ have the same meanings as in formula (VIIIf).

The compounds of formula (VIII) having the particular structure:

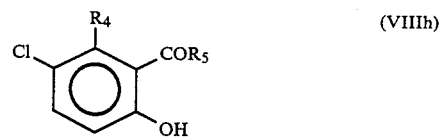

(VIIIh)

in which $R_4$ and $R_5$ have the same meanings as in formula (VIIIe) are obtained by the action of chlorine, at −20° C., in a carbon tetrachloride medium on the compounds of formula (VIIIg).

The compounds of formula (VIII) having the particular structure:

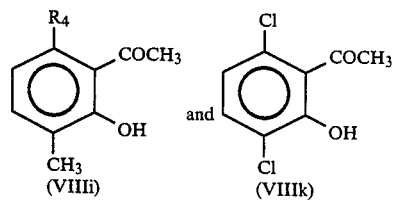

(VIIIi)   (VIIIk)

in which $R_4$ has the same meanings as in formula (1) are prepared according to the method described in Chem. Abst. 83, 9792f.

The compounds of formula (VIII) having the particular structure:

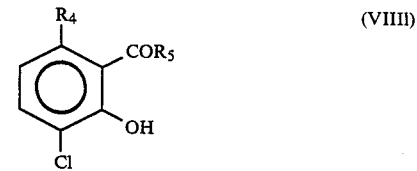

(VIIIl)

in which $R_4$ and $R_5$ have the same meanings as in formula (VIIIe) are obtained by the action of sodium nitrite in a dilute sulfuric acid medium followed by the action of cuprous chloride and hydrochloric acid, on the compounds of formula:

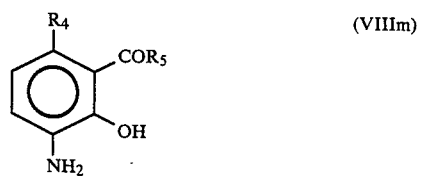

(VIIIm)

where $R_4$ and $R_5$ have the same meanings as in formula (VIIIl), the compounds of formula (VIIIm) being obtained according to the method described in J.C.S., 1963, 2374.

The compound of formula (XIIIa) for which $R_5$ represents the isopropyl group is prepared like the compound of formula (XIIIa) for which $R_5=CH_3$ (see J.C.S. 1973, 240) but from the corresponding reagents.

The compounds of formula (XV) are obtained by treating with acid chlorides or anhydrides of formula $R_5COCl$ or $(R_5CO)_2O$ where $R_5$ has the same meanings as in formula (XV) in the presence of a basic agent (pyridine or triethylamine for example) and in solution in an aprotic solvent (methylene chloride, for example), the corresponding hydroquinone derivatives.

Finally, the compounds of formula (XVIII) are obtained by methylation with methyl sulfate in the presence of a base (NaOH or $K_2CO_3$), of the corresponding hydroxylated compounds. These latter are obtained, like 5-acetyl 8-hydroxy benzodioxanne-1,4 (FRIES reaction, see Chem. Abst. 65, 2251 h) but from the corresponding reagents.

The salts of the derivatives of formula (I) are obtained in a conventional way and, for example, by the action of a mineral or organic acid in solution in an appropriate solvent, on said derivatives of formula (I) also in solution in an appropriate solution.

The following preparations are given by way of non limiting examples to illustrate the invention.

EXAMPLE 1

3-parahydroxyphenyl 1-[4-chloro 2-(2-piperidino)ethoxy]phenyl propanone-1 (I)

Code number: 87

To a solution of 9.6 g of 3-parahydroxyphenyl 1-[4-chloro 2-(2-piperidino)ethoxy]phenyl propen-2 one-1 [(II, code number 114, prepared according to the method described in example 10], in 100 ml of ethanol, are added 2 g of Raney nickel then a hydrogen stream is passed therethrough. After 12 hours under hydrogen, the mixture is filtered, the precipitate is washed with acetone and the filtrates evaporated. The residue is chromatographed on a silica column (medium pressure liquid chromatography; eluent: methylene chloride 95%-methanol 5%) and 6 g (yield: 62%) of the expected product are obtained.

By the same process, but from the corresponding reagents, the compounds of formula (I) are obtained appearing in Table I under the code numbers 1, 2 and 61.

EXAMPLE 2

3-parahydroxyphenyl 1-[4-chloro 3,6-dimethoxy 2-(2-piperidino)ethoxy]phenyl propanone-1 (I)

Code number: 61

A solution of 9.5 g of 3-parabenzyloxyphenyl 1-[4-chloro 3,6-dimethoxy 2-(2-piperidino)ethoxy]phenyl propen-2 one-1 [(II, code number 100] in 200 ml of alcohol and 18 ml of ~4N hydrochloric ethanol in the presence of 1 g of 10% palladium on charcoal is hydrogenated at room temperature and under a hydrogen pressure of $120·10^2$ Pa. Then the mixture is filtered, the filtrate evaporated, the residue taken up in chloroform, the solution obtained is neutralized with ammonia, decanted, the organic phase is dried on sodium sulfate, filtered and the filtrate evaporated. The residue is chromatographed on a silica column (medium pressure liquid chromatography; eluent: chloroform 95%-methanol 5% mixture) and thus 4.5 g (yield: 60%) of the expected product are obtained.

By the same process but from the corresponding reagents, the compounds of formula (I) are obtained shown in Table I under code numbers 1, 2 and 87.

EXAMPLE 3

3-parahydroxyphenyl 1-[3,6-dichloro 2-(2-piperidino)ethoxy]phenyl propanol-1 (I)

Code number: 75

A mixture of 8.4 g of 3-parahydroxyphenyl 1-[3,6-dichloro 2-(2-piperidino)ethoxy]propen-2 one-1 [(II), code number 113], 3.8 g of sodium borohydride, 8 ml of pyridine and 2 g of NaOH pellets in 150 ml of ethanol is brought to reflux for 1 h 30 minutes. Then, the mixture is diluted with iced water and hydrochloric acid, neutralized with ammonia, extracted with ethyl acetate, the organic phase is washed with water, dried on sodium sulfate, filtered and the filtrate evaporated. The residue is chromatographed on a silica column (medium pressure liquid chromatography; eluents: pure chloroform, then a chloroform 98%-methanol 2% mixture) and thus 6.2 g (yield: 74%) of the expected product are obtained.

By the same process, but from the corresponding reagents, the compounds of formula (I) are obtained shown in Table I under code numbers 3 to 23, 62 to 74, 76, 82 to 86, 89 and 92.

EXAMPLE 4

3-parahydroxyphenyl 2,2-dimethyl 1-[2-(2-piperidino)ethoxy]phenyl propanone-1 chlorhydrate (I)

Code number: 77

A mixture of 11.8 g of 3-parahydroxyphenyl 2,2-dimethyl 1-[2-(2-piperidino)ethoxy]phenyl propanone-1 [(I), code number 81] and 1.7 g of sodium borohydride in 200 ml of ethanol is left at room temperature for 12 hours; then 1.2 g of sodium borohydride and 2 drops of concentrated NaOH are added and the mixture is brought to reflux for 5 hours. Then the solvent is evaporated, the residue is taken up in dilute hydrochloric acid, the obtained solution is extracted with ether, washed with water, dried on sodium sulfate, filtered and the filtrate evaporated. After re-crystallization in pentane, 8 g of the expected compound (in base form) are obtained with a melting point of 80° C. It is dissolved in ether, hydrochloric ethanol is added and the precipitate obtained is filtered (yield: 54%) which corresponds to the expected salt.

By the same process, but from the corresponding reagents, the compounds of formula (I) are obtained, shown in Table I under code numbers 3 to 23, 62 to 76, 78, 82 to 86, 88 to 90 and 92.

EXAMPLE 5

3-parahydroxyphenyl 1-[3-(2-piperidino)ethoxy 1,4-dimethoxy naphtalenyl-2]propanol-1, hydrated (I)

A suspension of 4.3 g of 3-parabenzyloxyphenyl 1-[3-(2-piperidino)ethoxy 1,4-dimethoxy naphtalenyl-2]propanol-1 [(I), code number 86] and 0.45 g of 10% palladium on charcoal in 500 ml of ethanol is hydrogenated for 15 hours at a hydrogen pressure of $5·10^5$ Pa. Then, the mixture is filtered, the filtrate is evaporated and the residue chromatographed on a silica column (eluent: chloroform). The product obtained is recrystalized in a mixture of ether and pentane, which leads to 1.4 g (yield: 40%) of the expected product.

By the same process bur from the corresponding reagents, the compounds of formula (I) are obtained, shown in Table I under code numbers 8 to 20, 23, 62 to 67, 69 to 77 and 88 to 92.

EXAMPLE 6

3-parabenzyloxyphenyl 1-[4-chloro 3,6-dimethoxy 2-(2-piperidino)ethoxy]phenyl propanol-1 (I)

Code number: 82

To a solution of 15.8 g of 3-parabenzyloxyphenyl 1-[4-chloro 3,6-dimethoxy 2-(2-piperidino)ethoxy]phenyl propen-2 one-1 [(II), code number 100] in 150 ml of ethanol and one or two drops of concentrated NaOH are added 5.6 g of sodium borohydride, then the mixture is brought to reflux for 30 minutes. Then, the mixture is diluted with water, extracted with chloroform, dried on sodium sulfate, filtered and the filtrate is evaporated. 15.9 g (yield ~100%) of the expected product (oil) are obtained.

By the same process but from the corresponding reagents, the compounds of formula (I) are obtained, appearing in Table I under code numbers 4 to 7, 21, 22 and 83 to 86.

EXAMPLE 7

3-parahydroxyphenyl 1-[4-chloro 3,6-dimethoxy 2-(2-piperidino)ethoxy]phenyl propane, oxalate (I)

Code number: 79

A solution of 1.7 g of 3-parahydroxyphenyl 1-[4-chloro 3,6-dimethoxy 2-(2-piperidino)ethoxy]phenyl propanone-1 [(I), code number 61], in 8 ml of trifluoroacetic acid is heated to 50° C., then 3 ml of triethylsilane are added and the mixture is brought to reflux for 42 hours. Then it is diluted with iced water, neutralized with ammonia, extracted with ethyl acetate, the extract is washed with water, dried on sodium sulfate, filtered and the filtrate evaporated and the residue is chromatographed on a silica column (medium pressure liquid chromatography; eluent: chloroform 99%-methanol 1% mixture). Thus a pure product is obtained which is dissolved in acetone. An acetone oxalic acid solution is added and the precipitate obtained [0.5 g-yield: 26%] which corresponds to the expected salt is separated by filtration.

By the same process but from the corresponding reagents the compound of formula (I) is obtained shown in Table I under code number 60.

EXAMPLE 8

3-parabenzyloxyphenyl 2,2-dimethyl 1-[2-(2-piperidino)ethoxy]phenyl propanone-1 (I)

Code number: 80

To a suspension of 1.5 g of 80% sodium hydride in 150 ml of THF are added 12.9 g of 1-[2-(2-piperidino)ethoxy]phenyl 2-methyl propanone-1 (III). They are left in contact for 30 minutes at 40° C. then 10.9 g of parabenzyloxy benzyl chloride (IV) are slowly added. The mixture is brought to reflux for 24 hours, then it is thrown into iced water, extracted with ether, the extract is washed with water, dried on sodium sulfate, filtered and the filtrate evaporated. Thus 15.7 g (yield: 72%) of the expected product (oil) are obtained, which crystallizes spontaneously.

EXAMPLE 9

3-parahydroxyphenyl 1-[3,6-dimethoxy 5-nitro 2-(2-piperidino)ethoxy]phenyl propen-2 one-1 (II)

Code number: 111

A solution of 6 g of para 3-(2-tetrahydropyranyl oxy)-phenyl 1-[3,6-dimethoxy 5-nitro 2-(2-piperidino)ethoxy]phenyl propen-2 one-1 [(IIa), code number 112] in ~2N dilute hydrochloric acid is left at room temperature for 24 hours; then it is neutralized with ammonia, extracted with chloroform, the extract is washed with water, dried on sodium sulfate, filtered and the filtrate is evaporated. 5.2 g of the expected product (oily) are obtained whose spectral characteristics are given in Table II.

EXAMPLE 10

3-parahydroxyphenyl 1-[3,6-dichloro 2-(2-piperidino)ethoxy]phenyl propen-2 one-1 (II)

Code number: 113

A mixture of 9.6 g of 3,6-dichloro 2-(2-piperidino)ethoxy acetophenone [(V), code number 142], 3.7 g of parahydroxybenzaldehyde and 12 ml of concentrated NaOH in 100 ml of ethanol is left at room temperature for 15 hours. Then it is diluted with iced water and hydrochloric acid, extracted with chloroform, the extract is dried on sodium sulfate, filtered and the filtrate evaporated, the residue is taken up in dilute hydrochloric acid, washed with water, basified with concentrated NaOH, washed with ether, the aqueous phase is re-acidified with concentrated hydrochloric acid, neutralized with ammonia, extracted with chloroform, the extract is dried on sodium sulfate, filtered and the filtrate is evaporated. 8.4 g of the expected crystallized product are obtained whose spectral characteristics are given in Table II.

By the same process but from the corresponding reagents, the compounds of formula (II) are obtained shown in Table II under code numbers 24 to 44, 100 to 112 and 114 to 118.

EXAMPLE 11

2-methyl 1-[2-(2-piperidino)ethoxy]phenyl propanone-1 (III)

Code number: 144

A mixture of 3 g of 1-(2-hydroxy)phenyl 2-methyl propanone-1 (VIII), 4 g of N-(2-chloro)ethyl piperidine chlorhydrate and 8.2 g of potassium carbonate in 50 ml of acetonitrile is brought to reflux for 3 hours. Then it is filtered, the filtrate is evaporated, the residue is taken up in 1N hydrochloric acid, washed with ether, basified with concentrated NaOH, extracted with ether, the extract is washed with water, dried on sodium sulfate, filtered and the filtrate evaporated. 4.7 g (yield: 85%) of the expected product (oily) are obtained whose spectral characteristics are given in Table III.

By the same process but from the corresponding reagents, the compounds of formula (V) or (III) are obtained, given in Table III under code numbers 45 to 54, 130 to 143 and 145 to 148.

EXAMPLE 12

1-[1,4-dimethoxy 3-(2-piperidino)ethoxy naphtalenyl-2]ethanone (V)

Code number: 136

A mixture of 7 g of 1-[1,4-dimethoxy 3-(2-chloro)ethoxy naphtanenyl-2]ethanone (X), 4.5 ml of piperidine, 3.4 g of sodium iodide and 6.2 g of potassium carbonate in 70 ml of acetonitrile is brought to reflux for 5 hours. Then it is diluted with iced water, washed with ether, the etherated phase extracted with 2N hydrochloric acid, the aqueous phases collected together and basified with concentrated potash. Said phases are extracted with chloroform, the extract is dried on sodium sulfate, filtered and the filtrate evaporated. Thus 5.1 g (yield: 65%) of the expected product (oily) are obtained whose spectral characteristics appear in Table III.

By the same process, but from the corresponding reagents, the compounds of formula (III) or (V) are obtained given in Table III under code numbers 45 to 54, 130 to 135 and 137 to 148.

EXAMPLE 13

3,6-diethoxy 2-hydroxy acetophenone (VIII)

A solution of 50 g of 3,6-diethoxy 2-benzyloxy acetophenone (XI) in 500 ml of ethanol is hydrogenolyzed at 40° C. under a hydrogen pressure of $4.10^5$ Pa, in the presence of 5 g of 10% palladium on charcoal. Then it is filtered and the filtrate is evaporated to obtain the expected product (crystalline).

Melting point: 64° C.
Yield: 99%.
NMR spectrum (CDCl$_3$) δ ppm=13.7, s (O$\underline{H}$); 6.2, d and 6.98, d (J=9 Hz): (2 benzenic H); 4.02, q ($\overline{J}$=7 Hz): (2 OC$\underline{H}_2$); 2.68, s (CO—C$\underline{H}_3$); 1.4 and 1.44, 2 t (J=7 Hz): (2

O$^\frown$C$\underline{H}_3$)

IR Spectrum (KBr): CO band at 1610 cm$^{-1}$.

EXAMPLE 14

5-chloro 3,6-dimethoxy 2-hydroxy acetophenone (VIIIa)

A solution of 10 g of 3,6-dimethoxy 2-hydroxy acetophenone (VIIIb), 7 g of N-chlorosuccinimide, a spatula tip of azobisisobutyronitrile (A.I.B.N.) and a spatula tip of iron in 100 ml of carbon tetrachloride is brought to reflux for 6 hours. Then it is filtered on celite, the filtrate is evaporated and the residue crystallized in alcohol to obtain 7 g of the expected product.

Melting point: 108° C.
Yield: 61%.
NMR spectrum (CDCl$_3$) δ ppm=13.3, s (O$\underline{H}$); 7, s (1 benzenic H); 3.85, s (20 C$\underline{H}_2$); 2.72, s (COC$\underline{H}_3$).

EXAMPLE 15

3,6-dimethoxy 2-hydroxy 5-nitro acetophenone (VIIIc)

To a solution of 5 g of 3,6-dimethoxy 2-hydroxy acetophenone (VIIIb) in 20 ml of acetic acid, cooled to 10° C., is slowly added, while maintaining the temperature at 10° C., a solution of 1.9 ml of nitric acid at 40° B (d=1.38) in 2 ml of acetic acid. The mixture is left for 30 minutes at 10° C., then the reaction mixture is poured into 100 ml of iced water, and the orangish yellow precipitate obtained is filtered. The precipitate is washed with petroleum ether and 3.1 g (yield: 52%) of the expected product are obtained.

Melting point: 120° C.
NMR spectrum (CDCl$_3$) δ ppm=11.5, s (O$\underline{H}$); 7.6, s (1 aromatic H); 3.98, s (2 OC$\underline{H}_3$); and 2.78, s ($\overline{\text{COCH}}_3$).

EXAMPLE 16

1-[3-(2-chloro)ethoxy 1,4-dimethoxy naphtalenyl-2]ethanone (XIIa)

To a solution, heated to 50° C., of 6.6 g of 1-[1,4-dihydroxy naphtalenyl-2]ethanone (XIIIa) and 10 ml of 2-chloro ethanol in 100 ml of ethyl acetate are added 10 g of cuprous chloride, 50 g of calcium sulfate and 100 ml of acetonitrile, then an oxygen stream is passed therethrough for 4 hours. The reaction medium si thrown into a solution of 26 g of dithionite (Na$_2$S$_2$O$_4$) and 10 g of sodium bicarbonate in 500 ml of water and 500 ml of ethyl acetate. The brown precipitate obtained is filtered on celite, the solution is decanted, the organic phase is dried on sodium sulfate and filtered and the filtrate is evaporated. 8.3 g of product are obtained which is dissolved in acetonitrile (125 ml) and 125 ml of methyl sulfate are added. The mixture is cooled to 12° C. and 93 g of potassium carbonate are slowly added while maintaining the temperature at 12° C. The reaction medium is left at −30° C. for 12 hours, then is diluted in ether, acidified with concentrated hydrochloric acid, ether is added, the mixture is decanted, the organic phase is dried on sodium sulfate, filtered, and the solvent evaporated in a good vacuum and the residue is chromatographed on a silica column (medium pressure liquid chromatography; eluent: hexane: 90%-ethyl acetate 10% mixture). Thus 14 g (yield: 35%) of the expected product (oily) are obtained.

NMR spectrum (CDCl$_3$) δ ppm=8.0 and 7.5, m (4 atomic protons); 4.35, t (O—C$\underline{H}_2$); 3.88 and 3.92, s (2 OC$\underline{H}_3$); 3.7, t (C$\underline{H}_2$—Cl); 2.6, s ($\overline{\text{—COCH}}_3$).

IR spectrum (microcell): CO band at $\overline{1702}$ cm$^{-1}$.

By the same process but from the corresponding reagents, the other compounds of formula (XIIa) as well as the compounds of formula (XII) are obtained for example 2-benzyloxy 3,6-diethoxy acetophenone.

Oil.
NMR spectrum (CDCl$_3$): 7.25, m (5 aromatic benzylic protons); 6.42 and 6.8, d (J=9 Hz) (2 aromatic protons); 5.02, s (C$\underline{H}_2$—φ); 3.85 and 3.98, q (J=7 Hz) (2 OC$\underline{H}_2$); 2.4, s (COC$\underline{H}_3$); 1.25 and 1.37, t (J=7 Hz) (2

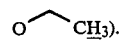

O$^\frown$C$\underline{H}_3$).

IR Spectrum (Microcell): CO band at 1703 cm$^{-1}$.

EXAMPLE 17

2,5-dihydroxy 4-fluoro acetophenone (XIII)

A mixture of 15 g of 1,4-diacetoxy 2-fluoro benzene (XV) and 19 g of aluminium chloride in 100 ml of nitrobenzene is heated to 140° C. for an hour. Then the mixture is thrown into 6N hydrochloric acid and ethyl acetate and the mixture obtained is decanted and the organic phase is dried on sodium sulfate. The residue is crystallized in isopropylic ether and 8 g (yield: 66%) of the expected product are obtained.

Melting point: 210° C.

NMR spectrum (DMSO) δ ppm=12.3, m and 11.3, m (2 OH); 7.45 and 6.8, d ($J_{H-F}$=10 Hz) (2 aromatic H); 2.62, s (COCH$_3$).

IR spectrum (KBr): CO band at 1640 cm$^{-1}$.

By the same process but from the corresponding reagents 1-(2,5-dihydroxy 4-chloro 4-phenyl) 2-methyl propanone-1 is obtained (Melting point 90° C.).

EXAMPLE 18

6-acetyl 5,8-dimethoxy 7-hydroxy benzodioxanne-1,4 (VIIId)

To 13.3 g of aluminium chloride, cooled to 0° C., is added drop by drop a solution of 23.8 g of 6-acetyloxy 5,8-dimethoxy benzodioxanne-1,4 (XVI) in 70 ml of 1,2-dichloro ethane. Then the mixture is heated at 60° C. for an hour and is poured in iced dilute hydrochloric acid. The obtained mixture is extracted with methylene chloride, then extracted with 1N aqueous NaOH, washed with methylene chloride, acidified with 2N hydrochloric acid, extracted with methylene chloride, the extract is dried on sodium sulfate, filtered, the filtrate is evaporated and the residue chromatographed on a silica column (medium pressure liquid chromatography; eluent: heptane 60%-ethyl acetate 40% mixture). Thus 7.5 g (yield: 30%) of the expected product are obtained.

Melting point: 112° C.

NMR spectrum (CDCl$_3$) δ ppm=13.0, s (OH); 4.3, m (—O—CH$_2$—CH$_2$—O—); 3.9, s (2 OCH$_3$); 2.6, s (COCH$_3$).

IR spectrum (KBr): CO band at 1630 cm$^{-1}$.

EXAMPLE 19

6-acetyloxy 5,8-dimethoxy benzodioxanne-1,4 (XVI)

To 122 ml of formic acid are added 27.5 ml of 36% hydrogen peroxid, drop drop by drop and at room temperature, the mixture is agitated for an hour and a solution of 60 g of 6-acetyl 5,8-dimethoxy benzodioxanne-1,4 (XVII) in 388 ml of formic acid is added while maintaining the temperature between −5° and −3° C. The mixture is left for 26 hours at 0° C., poured into 1200 ml of iced water, the precipitate formed is filtered, taken up in methylene chloride, the solution obtained is washed with water, dried on sodium sulfate, filtered and the filtrate is evaporated. Thus 38 g (yield: 60%) of the expected crystallized product is obtained which is washed in ether.

Melting point: 102° C.

| NMR spectrum (CDCl$_3$) δ ppm | = 6.2, s (1 aromatic H) |
|---|---|
| | = 4.3, s (O—CH$_2$—CH$_2$—O—) |
| | = 3.8, s (2 OCH$_3$) |
| | = 2.3, s (OCOCH$_3$) |

EXAMPLE 20

6-acetyl 5,8-dimethoxy benzodioxanne-1,4 (XVII)

1st step: 5-acetyloxy 8-methoxy benzodioxanne-1,4: obtained from 5-acetyl 8-methoxy benzodioxanne-1,4 (XVIII) in accordance with the procedure described in example 19.

Melting point: 121° C.
Yield: 74%.

NMR spectrum (CDCl$_3$) δ ppm=6.5, m (2 aromatic protons); 4.2, s (—O—CH$_2$—CH$_2$—O—); 3.8, s (OCH$_3$); 2.2, s (—OCOCH$_3$).

IR spectrum: COO band at 1765 cm$^{-1}$.

2nd step: 6-acetyl 5-hydroxy 8-acetyloxy benzodioxanne-1,4

To a suspension of 133.3 g of aluminium chloride in 150 ml of methylene chloride, cooled to 10° C., is added a solution of 112.1 g of 5-acetyloxy 8-methoxy benzodioxanne-1,4 in 350 ml of methylene chloride, then it is heated to reflux and 71.5 g of acetyl chloride are added while maintaining to reflux. Then it is left at reflux for two hours. After cooling, the liquid phase is eliminated and the solid residue taken up in a mixture of iced water and methylene chloride; after dissolving, the solution is filtered, the filtrate is evaporated and the residue crystallized in ethyl acetate, which leads to 87 g (yield: 69%) of the expected product.

Melting point: 138° C.

NMR spectrum (CDCl$_3$) δ ppm=14.3, s (OH); 7, s (1 aromatic proton); 4.3, s (O—CH$_2$—CH$_2$—O—); 2.5, s (COCH$_3$); 2.2, s (OCOCH$_3$).

IR spectrum (KBr) CO band at 1640 cm$^{-1}$, COO band at 1770 cm$^{-1}$.

3rd step: 6-acetyl 8-acetyloxy 5-methoxy benzodioxanne-1,4

To a suspension of 257.4 g of 6-acetyl 8-acetyloxy 5-hydroxy benzodioxanne-1,4 obtained in the preceding step and 552 g of potassium carbonate in 2500 ml of acetone are slowly added 189 ml of methyl sulfate. The mixture is filtered, the filtrate is evaporated, the residue is taken up in methylene chloride, the solution obtained is washed with a dilute NaOH solution, dried on sodium sulfate, filtered and the filtrate evaporated. Thus 265 g (Yield: 98%) of the expected (oily) product are obtained.

NMR spectrum (CDCl$_3$) δ ppm=7.1, s (1 aromatic H); 4.4, s (O—CH$_2$—CH$_2$—O—); 3.9, s (OCH$_3$); 2.6, s (COCH$_3$); 2.2, s (OCOCH$_3$).

IR spectrum (Microcell) CO band at 1675 cm$^{-1}$, COO band at 1770 cm$^{-1}$.

4th step: 6-acetyl 8-hydroxy 5-methoxy benzodioxanne-1,4

A suspension of 2.6 g of 6-acetyl 3-acetyloxy 5-methoxy benzodioxanne-1,4 and 4 g of potassium carbonate in 20 ml of methanol is left for an hour in contact under nitrogen. Then the mixture is filtered and the filtrate evaporated, the yellow precipitate obtained is taken up in concentrated hydrochloric acid, the precipitate obtained is filtered and washed with water on the filter. 1.4 g (yield: 63%) of the expected product is obtained.

Melting point: 86° C.

NMR spectrum (CDCl$_3$) δ ppm=6.9, s (1 aromatic H); 5.7, s (OH); 4.3, s (O—CH$_2$—CH$_2$—O—); 3.8, s (OCH$_3$); 2.5, s (COCH$_3$).

IR spectrum (KBr): CO band at 1640 cm$^{-1}$.

5th step: 6-acetyl 5,8-dimethoxy benzodioxanne-1,4 (XVII): obtained according to the process described in step 3 above but from 6-acetyl 8-hydroxy 5-methoxy benzodioxanne-1,4

Melting point: 123° C.
Yield: 73%.

NMR spectrum (CDCl$_3$) δ ppm=6.9, s (1 aromatic H); 4.3, s (O—CH$_2$—CH$_2$—O—); 3.9, s (2 OCH$_3$); 2.5, s (COCH$_3$).

IR spectrum (KBr): CO band at 1650 cm$^{-1}$.

EXAMPLE 21

3,5-dichloro 2-hydroxy 6-methoxy acetophenone (VIIIf)

Through a suspension of 1.7 g of 2-hydroxy 6-methoxy acetophenone (VIIIg) in 10 ml of chloroform is passed a chlorine gas stream at room temperature. Then, after 30 minutes, the mixture is washed with an aqueous sodium thiosulfate solution, dried on sodium sulfate, filtered and the filtrate evaporated. The residue is crystallized in isopropylic ether. Thus, 1 g (Yield: 50%) of the expected product is obtained (Melting point: 99° C.).

EXAMPLE 22

5-chloro 2-hydroxy 6-methoxy acetophenone (VIIIh)

Through a suspension of 16.6 g of 2-hydroxy 6-methoxy acetophenone (VIIIg) in 100 ml of carbon tetrachloride, cooled to −20° C., is passed a chlorine gas stream. Then, after an hour, the mixture is washed with an aqueous sodium thiosulfate solution, extracted with ether, the extract is dried on sodium sulfate, filtered, the filtrate is evaporated and the residue distilled. 12.4 g (Yield: 62%) of the expected product are obtained (Bp $_{2\,mm\,Hg}$=120° C.). The product crystallizes at rest (Melting point: 30° to 35° C.).

EXAMPLE 23

4,5-dichloro 3,6-dimethoxy 2-hydroxy acetophenone (VIIIe)

Prepared in accordance with the procedure described in example 21 but from 4-chloro 3,6-dimethoxy 2-hydroxy acetophenone (VIIIn) the expected product is obtained (Melting point: 96° C.) with a yield of 57%.

EXAMPLE 24

3-chloro 2-hydroxy 6-methoxy acetophenone (VIIIl)

To a solution of 12 g of 3-amino 2-hydroxy 6-methoxy acetophenone (VIIIm) in 150 ml of 20% sulfuric acid is added a solution of 15 g or sodium nitrite in 120 ml of water, while cooling to 0° C. It is left for 30 minutes at 0° C., then the reaction medium is added to a suspension of 24 g of cuprous chloride in 420 ml of 2N hydrochloric acid heated to 100° C. The mixture obtained is left for an hour at 100° C., then it is thrown into iced water and extracted with ether. The extract is dried on sodium sulfate, filtered and the filtrate evaporated. The residue is chromatographed on a silica column (medium pressure liquid chromatography; eluent: methylene chloride). Thus 6.8 g (Yield: 37%) of the expected product is obtained which melts at 82° C.

TABLE I $$\underset{\text{Ar}}{\underset{|}{\text{(R)}_n\text{-C}_6\text{H}_4}}-A-Ar-O-(CH_2)_m-N\begin{matrix}R_1\\R_2\end{matrix} \quad (I)$$

| Code No. | —A— | (R)$_n$ | m | $-N\begin{smallmatrix}R_1\\R_2\end{smallmatrix}$ | Ar—O— | Empirical formula | Molecular weight | Melting point (°C.) | Form | Elementary analysis or NMR spectrum % C H N |
|---|---|---|---|---|---|---|---|---|---|---|
| 1 | —CO—CH$_2$—CH$_2$— | 4-OH | 2 | piperidinyl | 3,5-dimethoxyphenyl (CH$_3$O, CH$_3$O) | C$_{24}$H$_{31}$NO$_5$ | 413.49 | 88 | Base | NMR(CDCl$_3$) δ ppm = 6.82, m and 6.10, s (6 aromatic H); 4.1, t (OCH$_2$); 3.72 and 3.8, s (2CH$_3$O); 2.4 to 3,m (10H: COCH$_2$CH$_2$ and $\text{CH}_2\text{—N}\begin{smallmatrix}\text{CH}_2\\\text{CH}_2\end{smallmatrix}$); 1.5, m (CH$_2$—CH$_2$—CH$_2$) |
| 2 | —CO—CH$_2$—CH$_2$— | 4-OH | 2 | piperidinyl | 2-methyl-3,5-dimethoxyphenyl | C$_{24}$H$_{32}$ClNO$_5$ | 449.96 | 181 | HCl | Cal. 64.06 7.17 3.11<br>Obt. 63.98 7.09 3.08 |
| 3 | —CH—CH$_2$—CH$_2$<br>   OH | H | 2 | piperidinyl | 2-methyl-3,5-dimethoxyphenyl | C$_{24}$H$_{33}$NO$_4$ | 399.51 | 79 | Base | Cal. 72.15 8.33 3.51<br>Obt. 72.04 8.51 3.45 |
| 4 | —CH—CH$_2$—CH$_2$<br>   OH | 4-F | 2 | piperidinyl | 2-methyl-3,5-dimethoxyphenyl | C$_{24}$H$_{32}$FNO$_4$ | 417.50 | Oil | Base | Cal. 69.04 7.73 3.36<br>Obt. 68.49 7.56 3.15 |

TABLE I-continued $$\text{Ar}\begin{array}{c}(R)_n\\ \diagdown\\ \diagup\\ A\end{array}\!\!\!\!\!\!\!\!\!\!\!\!\!\!\!\!\!\!\!\!\!\!\!\!\!\bigcirc\!\!\!-\!\!O\!-\!(CH_2)_m\!-\!N\!\!\begin{array}{c}R_1\\ \diagdown\\ R_2\end{array}\quad (I)$$

| Code No. | —A— | (R)$_n$ | m | —N(R$_1$)(R$_2$) | Ar—O— | Empirical formula | Molecular weight | Melting point (°C.) | Form | Elementary analysis or NMR spectrum % C H N |
|---|---|---|---|---|---|---|---|---|---|---|
| 5 | —CH—CH$_2$—CH$_2$—<br>\|<br>OH | 4-Cl | 2 | piperidine | 2-OCH$_3$, 3-CH$_3$, 4-OCH$_3$ phenyl | C$_{24}$H$_{32}$ClNO$_4$ | 433.96 | Oil | Base | Cal. 66.42 7.43 3.23<br>Obt. 65.80 7.95 3.34 |
| 6 | —CH—CH$_2$—CH$_2$—<br>\|<br>OH | 4-CH$_3$ | 2 | piperidine | 2-OCH$_3$, 3-CH$_3$, 4-OCH$_3$ phenyl | C$_{25}$H$_{35}$NO$_4$ | 413.54 | Oil | Base | Cal. 72.61 8.53 3.39<br>Obt. 72.31 8.58 3.27 |
| 7 | —CH—CH$_2$—CH$_2$—<br>\|<br>OH | 4-CH$_3$O | 2 | piperidine | 2-OCH$_3$, 3-CH$_3$, 4-OCH$_3$ phenyl | C$_{25}$H$_{35}$NO$_5$ | 429.54 | Oil | Base | Cal. 69.90 8.21 3.26<br>Obt. 69.25 8.33 3.14 |
| 8 | —CH—CH$_2$—CH$_2$—<br>\|<br>OH | 2-OH | 2 | piperidine | 2-OCH$_3$, 3-CH$_3$, 4-OCH$_3$ phenyl | C$_{24}$H$_{34}$ClNO$_5$ +<br>4% H$_2$O | 470.81 | 88 | HCl +<br>4% H$_2$O | Cal. 61.22 7.73 2.98<br>Obt. 61.50 7.93 2.97 |

TABLE I-continued (I) [structure: Ar—O—(CH₂)ₘ—N(R₁)(R₂) with A bridge and (R)ₙ on Ar ring]

| Code No. | —A— | (R)ₙ | m | —N(R₁)(R₂) | Ar—O— | Empirical formula | Molecular weight | Melting point (°C.) | Form | | Elementary analysis or NMR spectrum % | C | H | N |
|---|---|---|---|---|---|---|---|---|---|---|---|---|---|---|
| 9 | —CH(OH)—CH₂—CH₂— | 3-OH | 2 | piperidine | 2,6-diOCH₃-3-CH₃-phenoxy | C₂₄H₃₃NO₅ | 415.52 | 128 | Base | Cal. Obt. | | 69.31 69.25 | 8.01 8.02 | 3.37 3.19 |
| 10 | —CH(OH)—CH₂—CH₂— | 4-OH | 2 | piperidine | 2,6-diOCH₃-3-CH₃-phenoxy | C₂₄H₃₃NO₅ | 415.52 | 142 | Base | Cal. Obt. | | 69.31 69.29 | 8.01 8.10 | 3.37 3.21 |
| 11 | —CH(OH)—CH₂—CH₂— | 4-OH | 3 | piperidine | 2,6-diOCH₃-3-CH₃-phenoxy | C₂₅H₃₅NO₅ | 429.54 | 118 | Base | Cal. Obt. | | 69.90 69.95 | 8.21 8.35 | 3.26 3.30 |
| 12 | —CH(OH)—CH₂—CH₂— | 4-OH | 2 | —N(Et)(Et) | 2,6-diOCH₃-3-CH₃-phenoxy | C₂₃H₃₃NO₅ | 403.50 | 90 | Base | Cal. Obt. | | 68.46 68.28 | 8.24 8.39 | 3.47 3.46 |

TABLE I-continued $$\text{(I)}$$

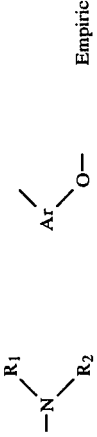

| Code No. | —A— | $(R)_n$ | m | $-N\begin{matrix}R_1\\R_2\end{matrix}$ | Ar—O— | Empirical formula | Molecular weight | Melting point (°C.) | Form | | % | Elementary analysis or NMR spectrum C | H | N |
|---|---|---|---|---|---|---|---|---|---|---|---|---|---|
| 13 | —CH—CH$_2$—CH$_2$—<br>\|<br>OH | 4-OH | 2 | 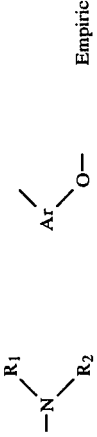 | 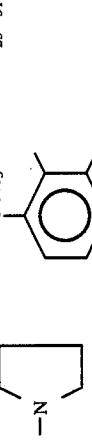 | C$_{23}$H$_{31}$NO$_5$ | 401.49 | 159 | Base | Cal.<br>Obt. | | 68.80<br>68.14 | 7.78<br>7.84 | 3.49<br>3.52 |
| 14 | —CH—CH$_2$—CH$_2$—<br>\|<br>OH | 4-OH | 2 | 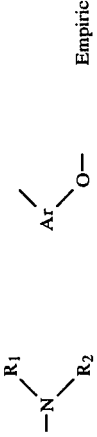 | 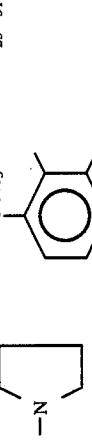 | C$_{25}$H$_{35}$NO$_6$ +<br>½ HOOC—COOH | 513.06 | 175 | ½ oxalate | Cal.<br>Obt. | | 62.03<br>61.89 | 7.17<br>7.32 | 2.73<br>2.73 |
| 15 | —CH—CH$_2$—CH$_2$—<br>\|<br>OH | 4-OH | 2 | 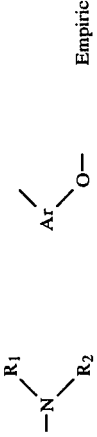 | 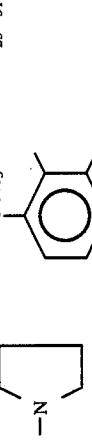 | C$_{25}$H$_{35}$NO$_6$ | 445.54 | 117 | Base | Cal.<br>Obt. | | 67.39<br>67.16 | 7.92<br>8.08 | 3.14<br>2.89 |
| 16 | —CH—CH$_2$—CH$_2$—<br>\|<br>OH | 4-OH | 2 | 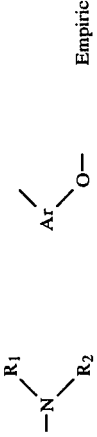 | 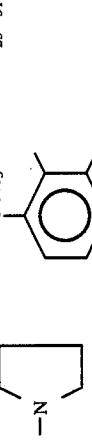 | C$_{24}$H$_{32}$NO$_6$ +<br>1.2% H$_2$O | 435.56 | 148 | 0.5 oxa-<br>late +<br>1.2%<br>H$_2$O | Cal.<br>Obt. | | 66.17<br>66.32 | 8.00<br>7.62 | 3.22<br>3.17 |

TABLE I-continued $$\begin{array}{c}(R)_n\\ \diagdown\\ Ar-A\diagup\\ \diagdown O-(CH_2)_m-N\diagup R_1\\ \diagdown R_2\end{array}\quad (I)$$

| Code No. | —A— | (R)ₙ | m | $-N\diagup^{R_1}_{R_2}$ | Ar—O— | Empirical formula | Molecular weight | Melting point (°C.) | Form | Elementary analysis or NMR spectrum % C H N |
|---|---|---|---|---|---|---|---|---|---|---|
| 17 | —CH—CH₂—CH₂—<br>\|<br>OH | 4-OH | 2 | morpholine | 2,3,5-trimethoxy-methylphenyl (OCH₃, OCH₃, OCH₃) | C₂₃H₃₁NO₆ | 417.49 | 107 | Base | Cal. 66.17 7.48 3.36<br>Obt. 65.88 7.70 3.47 |
| 18 | —CH—CH₂—CH₂—<br>\|<br>OH | 4-OH | 2 | $-N(CH_3)_2$ | 2,3,5-trimethoxy-methylphenyl | C₂₁H₂₉NO₅ +<br>1.1% H₂O | 379.70 | 105 | Base +<br>1.1%<br>H₂O | Cal. 66.43 7.83 3.69<br>Obt. 66.03 7.98 3.86 |
| 19 | —CH—CH₂—CH₂—<br>\|<br>OH | 4-OH | 2 | $-N(Et)_2$ | 3,4,5-trimethoxy-methylphenyl | C₂₄H₃₅NO₆ | 433.53 | 112 | Base | Cal. 66.49 8.14 3.23<br>Obt. 66.40 8.48 2.93 |
| 20 | —CH—CH₂—CH₂—<br>\|<br>OH | 4-OH | 2 | $-N(Et)_2$ | 2,3-dimethoxy-methylphenyl | C₂₅H₃₃NO₈ +<br>1.7% H₂O | 483.75 | 103 | Oxa-<br>late +<br>1.7%<br>H₂O | Cal. 62.07 7.07 2.90<br>Obt. 62.24 7.14 3.04 |

TABLE I-continued

General formula (I):

Ar—A—O—(CH$_2$)$_m$—N(R$_1$)(R$_2$), with (R)$_n$ on Ar ring

| Code No. | —A— | (R)$_n$ | m | —N(R$_1$)(R$_2$) | Ar—O— | Empirical formula | Molecular weight | Melting point (°C.) | Form | Elementary analysis or NMR spectrum |
|---|---|---|---|---|---|---|---|---|---|---|
| 21 | —CH(OH)—CH$_2$—CH$_2$— | 4-O—CH$_2$—φ | 2 | piperidine | 3,5-di-OCH$_3$, 4-CH$_3$O phenyl (trimethoxy-methyl phenyl) | C$_{31}$H$_{39}$NO$_5$ | 505.63 | Oil | Oxalate + 1.7% H$_2$O | NMR(CDCl$_3$) δ ppm = 6.8 to 7.5, m (9 aromatic H); 6.25, s (2 aromatic H in 3 and 5); 5.05, s (OCH$_2$—φ); 5.1, m (CH—O); 4.1, m (OH and OCH$_2$); 3.8, s (2CH$_3$O); 2 to 2.8, m (10H: —CH$_2$—CH$_2$—N—CH$_2$—CH$_2$— and CH$_2$—N—CH$_2$); 1.4 to 1.8, m (CH$_2$—CH$_2$—CH$_2$) |
| 22 | —CH(OH)—CH$_2$—CH$_2$— | 3,4-di-O—CH$_2$—φ | 2 | piperidine | 2-OCH$_3$, 3-CH$_3$, 4,6-di-OCH$_3$ phenyl | C$_{38}$H$_{45}$NO$_6$ | 611.75 | Oil | Base | NMR(CDCl$_3$) δ ppm = 7.2 to 7.6, m (10 benzylic H); 6.6 to 6.9, m (5 aromatic H); 5.1, s (2OCH$_2$φ); 5 to 5.3., m (OH and CH—O); 4.4 and 3.4, m (OCH$_2$); 3.7 and 3.78, s (2CH$_3$O); 2.2 to 2.6, m and 1.4 to 1.8, m (CH$_2$CH$_2$ and CH$_2$—N) |
| 23 | —CH(OH)—CH$_2$—CH$_2$— | 3,4-diOH | 2 | piperidine | 2-OCH$_3$, 3-CH$_3$, 4,6-di-OCH$_3$ phenyl | C$_{24}$H$_{34}$ClNO$_6$ + 4.8% H$_2$O | 491.57 | 140 | HCl + 4.8% H$_2$O | C H N<br>Cal. 58.63 7.51 2.85<br>Obt. 58.66 7.42 2.67 |

TABLE I

| Code No. | Ar—O— | —A— | (R)ₙ | m | $\overset{R_1}{\underset{R_2}{-N}}$ | Form | Empirical Formula | Molecular weight | Melting point (°C.) | ELEMENTARY ANALYSIS or NMR spectrum % | C | H | N |
|---|---|---|---|---|---|---|---|---|---|---|---|---|---|
| 60 | 3,5-dimethoxy-phenyl (OCH₃, OCH₃) | —(CH₂)₃— | OH | 2 | piperidinyl | Base | C₂₄H₃₃NO₄ | 399.51 | 136 | Cal. Obt. | 72.15 71.94 | 8.33 8.44 | 3.51 3.38 |
| 61 | 2,3-dimethoxy-6-chlorophenyl | —CO—CH₂—CH₂— | OH | 2 | piperidinyl | Base | C₂₄H₃₀ClNO₅ | 447.94 | 120 | Cal. Obt. | 64.35 64.22 | 6.75 6.96 | 3.13 2.94 |
| 62 | 2,3-dimethoxyphenyl | —CH(OH)—CH₂—CH₂— | OH | 2 | pyrrolidinyl | Base | C₂₅H₃₇NO₅ | 431.55 | 75 | Cal. Obt. | 69.57 69.19 | 8.64 8.82 | 3.25 3.51 |
| 63 | 2,3-dimethoxyphenyl | —CH(OH)—CH₂—CH₂— | OH | 2 | cyclopentyl-NH— | Oxalate | C₂₆H₃₅NO₉ | 505.55 | 197 | Cal. Obt. | 61.77 61.52 | 6.98 7.36 | 2.77 2.88 |

TABLE I-continued $$\text{Ar}\diagdown_{O}\diagup^{A}\diagdown\underset{\text{(R)}_n}{\bigcirc}-O-(CH_2)_m-N\diagup^{R_1}_{R_2} \qquad (I)$$

| Code No. | Ar—O— | —A— | (R)$_n$ | m | $\text{—N}\diagup^{R_1}_{R_2}$ | Form | Empirical Formula | Molecular weight | Melting point (°C.) | | ELEMENTARY ANALYSIS or NMR spectrum | | |
|---|---|---|---|---|---|---|---|---|---|---|---|---|---|
| 64 | 2,5-(OCH$_3$)$_2$, 4-OCH$_3$ phenyl | —CH(OH)—CH$_2$— | OH | 2 | piperidine | Base | C$_{24}$H$_{33}$NO$_5$ | 415.51 | 128 | Cal. Obt. | 69.37 68.86 | 8.01 8.00 | 3.37 3.36 |
| 65 | 2,4-(OEt)$_2$, 3-OCH$_3$ phenyl | —CH(OH)—CH$_2$— | OH | 2 | N,N-diethyl | Base | C$_{25}$H$_{37}$NO$_5$ | 431.55 | 80 | Cal. Obt. | 69.57 69.07 | 8.64 8.77 | 3.25 3.44 |
| 66 | 2,3-(OCH$_3$)$_2$, 4,5-(O-CH$_2$CH$_2$-O) phenyl | —CH(OH)—CH$_2$— | OH | 2 | piperidine | Base | C$_{26}$H$_{35}$NO$_7$ | 473.55 | 158 | Cal. Obt. | 65.94 65.63 | 7.45 7.39 | 2.96 2.82 |
| 67 | 3,5-(OCH$_3$)$_2$, 2,4-(OCH$_3$)$_2$ phenyl | —CH(OH)—CH$_2$— | OH | 2 | piperidine | Chlorhydrate | C$_{26}$H$_{38}$ClNO$_7$ | 512.03 | 105 | Cal. Obt. | 60.98 60.65 | 7.48 7.79 | 2.74 2.91 |

TABLE I-continued $$\text{Ar}-\text{O}-\overset{\displaystyle (R)_n}{\underset{\displaystyle A}{\bigcirc}}-\text{O}-(CH_2)_m-N\overset{R_1}{\underset{R_2}{}} \quad (I)$$

| Code No. | Ar—O— | —A— | (R)ₙ | m | $-N\overset{R_1}{\underset{R_2}{}}$ | Form | Empirical Formula | Molecular weight | Melting point (°C.) | | ELEMENTARY ANALYSIS or NMR spectrum | | |
|---|---|---|---|---|---|---|---|---|---|---|---|---|---|
| 68 | naphthyl with OCH₃, OCH₃, OCH₃ | —CH(OH)—CH₂— | OH | 2 | piperidine (—N⟨(CH₂)₅⟩) | Base + 0.8% H₂O | C₂₈H₃₅NO₅ + 0.8% H₂O | 469.32 | 180 | Cal. Obt. | 71.65 71.47 | 7.61 7.84 | 2.99 2.91 |
| 69 | phenyl with OCH₃, OCH₃, OCH₃, Cl | —CH(OH)—CH₂— | OH | 2 | piperidine | Base Oxalate | C₂₄H₃₂ClNO₅ C₂₆H₃₄ClNO₉ | 449.96 539.99 | 116 131 | Cal. Obt. | (Oxalate) 57.83 57.67 | 6.35 6.47 | 2.59 2.88 |
| 70 | phenyl with OCH₃, OCH₃, OCH₃, Cl | —CH(OH)—CH₂— | OH | 2 | —N(Et)₂ | base | C₂₃H₃₂ClNO₅ | 437.95 | 124 | Cal. Obt. | 63.07 62.80 | 7.37 7.46 | 3.20 3.23 |
| 71 | phenyl with OCH₃, OCH₃, OCH₃, Cl | —CH(OH)—CH₂— | OH | 2 | —N(iPr)₂ | Base | C₂₅H₃₆ClNO₅ | 466.00 | 102 | Cal. Obt. | 64.43 64.51 | 7.79 8.05 | 3.01 2.98 |

TABLE I-continued $$\text{Ar-CH}_2\text{-O-(CH}_2)_m\text{-N}\begin{matrix}R^1\\R_2\end{matrix} \quad \text{(with }(R)_n\text{ on phenyl, A linker)} \tag{I}$$

| Code No. | Ar—O— | —A— | (R)ₙ | m | —N(R₁)(R₂) | Form | Empirical Formula | Molecular weight | Melting point (°C.) | ELEMENTARY ANALYSIS or NMR spectrum | | | |
|---|---|---|---|---|---|---|---|---|---|---|---|---|---|
| 72 | 4-F, 2,6-di-OCH₃ phenyl | —CH(OH)—CH₂— | OH | 2 | piperidine | Base | C₂₄H₃₂FNO₅ | 433.50 | 122 | Cal.<br>Obt. | 66.49<br>66.43 | 7.44<br>7.53 | 3.23<br>3.01 |
| 73 | 4-Cl, 2,6-di-OCH₃ phenyl | —CH(OH)—CH₂— | OH | 2 | piperidine | Base | C₂₄H₃₂ClNO₅ | 449.96 | — | Cal.<br>Obt. | 64.06<br>63.95 | 7.17<br>6.89 | 3.11<br>2.83 |
| 74 | 4-NO₂, 2,6-di-OCH₃ phenyl | —CH(OH)—CH₂— | OH | 2 | piperidine | Base | C₂₄H₃₂N₂O₇ | 460.51 | 162 | Cal.<br>Obt. | 62.59<br>62.84 | 7.00<br>7.40 | 6.08<br>5.99 |
| 75 | 3,5-di-Cl, 2-OCH₃ phenyl | —CH(OH)—CH₂— | OH | 2 | piperidine | Base | C₂₂H₂₇Cl₂NO₃ | 424.36 | 147 | Cal.<br>Obt. | 62.26<br>62.41 | 6.41<br>6.60 | 3.30<br>3.25 |

TABLE I-continued (I)

| Code No. | Ar—O— | —A— | (R)$_n$ | m | $\begin{array}{c}R_1\\\phantom{N}\\N\\\phantom{N}\\R_2\end{array}$ | Form | Empirical Formula | Molecular weight | Melting point (°C.) | ELEMENTARY ANALYSIS or NMR spectrum | | |
|---|---|---|---|---|---|---|---|---|---|---|---|---|
| 76 | 2-methoxy-4-chlorophenoxy | —CH(OH)—CH$_2$—CH$_2$— | OH | 2 | piperidine | Base | C$_{22}$H$_{28}$ClNO$_3$ | 389.91 | 153 | Cal. Obt. | 67.76 67.74 | 7.24 7.41 | 3.59 3.58 |
| 77 | 2-methoxyphenoxy | —C(OH)(CH$_3$)$_2$—CH$_2$— | OH | 2 | piperidine | HCl | C$_{24}$H$_{34}$ClNO$_3$ | 419.98 | 210 | Cal. Obt. | 68.63 68.72 | 8.16 8.10 | 3.34 3.32 |
| 78 | 2,6-dimethoxy-4-chlorophenoxy | —CH(OH)—CH$_2$—CH$_2$— | H | 2 | piperidine | base | C$_{24}$H$_{32}$ClNO$_4$ | 433.96 | 89 | Cal. Obt. | 66.42 66.50 | 7.43 7.51 | 3.23 3.29 |
| 79 | 2,6-dimethoxy-4-chlorophenoxy | —(CH$_2$)$_3$— | OH | 2 | piperidine | Oxalate | C$_{26}$H$_{34}$ClNO$_8$ | 523.99 | 164 | Cal. Obt. | 59.59 59.73 | 6.54 6.43 | 2.67 2.96 |
| 80 | 2-methoxyphenoxy | —CO—C(CH$_3$)$_2$—CH$_2$— | OCH$_2$φ | 2 | piperidine | Base | C$_{31}$H$_{37}$NO$_3$ | 471.61 | <50 | NMR (CDCl$_3$) δ ppm = 6.6 to 7.4, m (13 aromatic H); 5.0, s (CH$_2$—φ); 4.0, t and 2.6, t (O—CH$_2$—CH$_2$); 2.85, s (CH$_2$); 2.4, m (4 piperidinic H); 1.4, m (6 piperidinic H); 1.15, s (2CH$_3$) | | |

TABLE I-continued (I)

| Code No. | Ar—O— | —A— | (R)$_n$ | m | $-N\begin{smallmatrix}R_1\\R_2\end{smallmatrix}$ | Form | Empirical Formula | Molecular weight | Melting point (°C.) | ELEMENTARY ANALYSIS or NMR spectrum |
|---|---|---|---|---|---|---|---|---|---|---|
| 81 | 2-methoxyphenoxy | —CO—C(CH₃)₂—CH₂— | OH | 2 | piperidine | Base | C₂₄H₃₁NO₃ | 381.49 | Oil | NMR (CDCl₃) δ ppm = 7.4, m (OH); 6.6 to 7.2, m (8 aromatic H); 4.05 and 2.6, t (O—CH₂—CH₂); 2.8, s (CH₂); 1.15, s (2CH₃); 2.5 and 1.55, m (10 piperidinic H). |
| 82 | 3-chloro-2,6-dimethoxyphenoxy | —CH(OH)—CH₂—CH₂— | OCH₂φ | 2 | piperidine | Base | C₃₁H₃₈ClNO₅ | 541.08 | Oil | NMR (CDCl₃) δ ppm = 7.4, s (5 benzylic H); 6.5 to 7.2, m (5 aromatic H); 5, s (OCH₂); 5.05, m (OH); 4.2, m (C—H / OH); 3.65 and 3.75, s (CH₃O); 3.7 and 2.7, m (OCH₂—CH₂); 2.4 and 1.5, m (10 piperidinic H) |
| 83 | 3-fluoro-2,6-dimethoxyphenoxy | —CH(OH)—CH₂—CH₂— | OCH₂φ | 2 | piperidine | Base | C₃₁H₃₈FNO₅ | 523.62 | Oil | NMR (CDCl₃) δ ppm = 7.4, s (5 benzylic H); 6.8, d and 7.10, d (4 aromatic H); 6.4, d (JH—F) (1 aromatic H); 5, s(CH₂); 5.05, m (CH—O); 4.5, 4.0 and 2.8, m (OCH₂CH₂—); 3.65 and 3.8, s (CH₃O); 2.4 and 1.6, m (10 piperidinic H) |
| 84 | 2,6-diethoxyphenoxy | —CH(OH)—CH₂—CH₂— | OCH₂φ | 2 | —N(Et)(Et) | base | C₃₂H₄₃NO₅ | 521.67 | Oil | NMR (CDCl₃) δ ppm = 7.35, s (5 benzylic H); 6.4 to 7.4, m (6 aromatic H); 5.35, m (OH); 5, s (CH₂); 4.45, m (CH—O); 3.6 to 4.10, m (3-OCH₂); 2.4 to 2.8, m (CH₂—CH₂— and N(CH₂)₂: 10 protons); 0.9 to 1.4, m (12H: 4CH₃) |

TABLE I-continued (I)

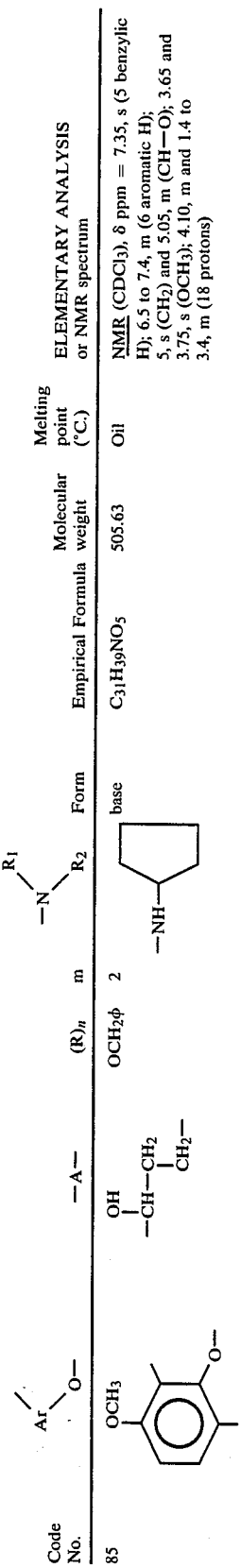
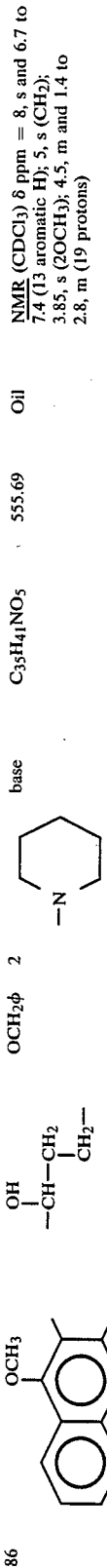
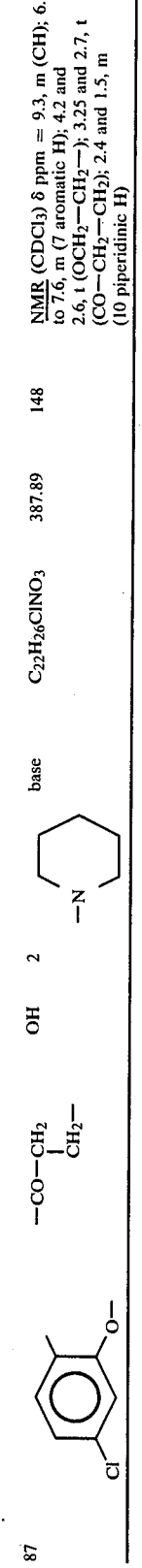
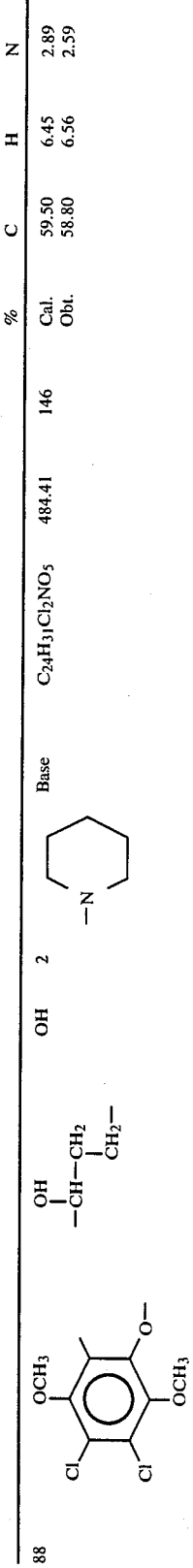

| Code No. | Ar | —A— | (R)$_n$ | m | R$_1$, R$_2$ —N | Form | Empirical Formula | Molecular weight | Melting point (°C.) | ELEMENTARY ANALYSIS or NMR spectrum |
|---|---|---|---|---|---|---|---|---|---|---|
| 85 | OCH$_3$ / OCH$_3$ (2,3-dimethoxy, methyl) | —CH—CH$_2$—CH$_2$— with OH | OCH$_2$φ | 2 | cyclopentyl-NH | base | C$_{31}$H$_{39}$NO$_5$ | 505.63 | Oil | NMR (CDCl$_3$), δ ppm = 7.35, s (5 benzylic H); 6.5 to 7.4, m (6 aromatic H); 5, s (CH$_2$) and 5.05, m (CH—O); 3.65 and 3.75, s (OCH$_3$); 4.10, m and 1.4 to 3.4, m (18 protons) |
| 86 | (naphthalene with OCH$_3$, CH$_3$, OCH$_3$) | —CH—CH$_2$—CH$_2$— with OH | OCH$_2$φ | 2 | piperidine | base | C$_{35}$H$_{41}$NO$_5$ | 555.69 | Oil | NMR (CDCl$_3$) δ ppm = 8, s and 6.7 to 7.4 (13 aromatic H); 5, s (CH$_2$); 3.85, s (2OCH$_3$); 4.5, m and 1.4 to 2.8, m (19 protons) |
| 87 | OCH$_3$ / Cl (methyl, methoxy, chloro) | —CO—CH$_2$—CH$_2$— | OH | 2 | piperidine | base | C$_{22}$H$_{26}$ClNO$_3$ | 387.89 | 148 | NMR (CDCl$_3$) δ ppm = 9.3, m (CH); 6.6 to 7.6, m (7 aromatic H); 4.2 and 2.6, t (OCH$_2$—CH$_2$—); 3.25 and 2.7, t (CO—CH$_2$—CH$_2$); 2.4 and 1.5, m (10 piperidinic H) |
| 88 | OCH$_3$ / Cl / Cl / OCH$_3$ (methyl, dimethoxy, dichloro) | —CH—CH$_2$—CH$_2$— with OH | OH | 2 | piperidine | Base | C$_{24}$H$_{31}$Cl$_2$NO$_5$ | 484.41 | 146 | % C H N<br>Cal. 59.50 6.45 2.89<br>Obt. 58.80 6.56 2.59 |

TABLE I-continued

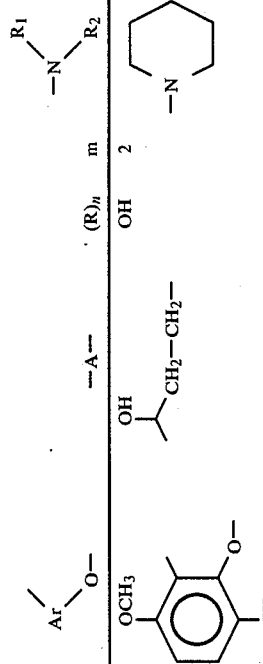
(I)

| Code No. | Ar—O— | —A— | (R)$_n$ | m | $-N\begin{matrix}R_1\\R_2\end{matrix}$ | Form | Empirical Formula | Molecular weight | Melting point (°C.) | ELEMENTARY ANALYSIS or NMR spectrum | | | |
|---|---|---|---|---|---|---|---|---|---|---|---|---|---|
| | | | | | | | | | | | % C | H | N |
| 89 | OCH$_3$, CH$_3$ on ring with OCH$_3$ and OCH$_3$ | —CH(OH)—CH$_2$—CH$_2$— | OH | 2 | piperidine | Base | C$_{24}$H$_{33}$NO$_4$ | 399.51 | Oil | NMR (CDCl$_3$) δ ppm = between 6.4 and 7.2, m (6 aromatic H); 5.7, s (OH and phenolic OH); 5.1, t (H in α of OH); 3.98, t (—OCH$_2$); 3.75, s (OCH$_3$); 2.2, s (CH$_3$); 2.4, m (CH$_2$—CH$_2$ and 3CH$_2$ in α of nitrogen H); 1.5, m (6 piperidinic H). | | | |
| 90 | OCH$_3$, Cl on ring with OCH$_3$ | —C(OH)(CH$_3$)—CH$_2$— | OH | 2 | piperidine | Base | C$_{26}$H$_{36}$ClNO$_5$ | 478.01 | 162 | Cal. Obt. | 65.32 64.77 | 7.59 5.62 | 2.93 2.68 |
| 91 | OCH$_3$, Cl on ring with OCH$_3$ | —CO—C(CH$_3$)—CH$_2$— | OH | 2 | piperidine | Base | C$_{26}$H$_{34}$ClNO$_5$ | 475.99 | 140 | Cal. Obt. | 65.60 65.08 | 7.20 7.24 | 2.94 2.67 |
| 92 | OCH$_3$, Cl on ring with OCH$_3$ | —CH(OH)—CH$_2$—CH$_2$— | OH | 2 | piperidine | Base | C$_{23}$H$_{30}$ClNO$_4$ | 419.93 | 126 | Cal. Obt. | 65.78 65.77 | 7.20 7.33 | 3.34 3.33 |

TABLE II (II) and (IIa)

$$\text{Ar}\underset{O-(CH_2)_m-N\begin{smallmatrix}R_1\\R_2\end{smallmatrix}}{\overset{CO-CH=CH-\underset{(R)_n}{\bigcirc}}{}}$$

| Code No. | $-N\begin{smallmatrix}R_1\\R_2\end{smallmatrix}$ | $(R)_n$ | m | $Ar\begin{smallmatrix}\diagup\\ O-\end{smallmatrix}$ | Empirical formula | Molecular weight | Melting point (°C.) | ELEMENTARY ANALYSIS NMR SPECTRUM I.R. SPECTRUM |
|---|---|---|---|---|---|---|---|---|
| 24 | —N(piperidine) | H | 2 | 2,3-dimethoxyphenoxy (OCH₃ positions) | $C_{24}H_{29}NO_4$ | 395,48 | Oil | NMR(CDCl$_3$)δppm=6.5 to 7.6 (7 aromatic H and CH=CH); 4.05,t(OC$\underline{H}_2$);3.7 and 3.85,s (2C$\underline{H}_3$O);2.6,t(C$\underline{H}_2$—N);2.4 and 1.5,m(N piperidine) |
| 25 | —N(piperidine) | 4-Cl | 2 | 2,3-dimethoxyphenoxy | $C_{24}H_{28}ClNO_4$ | 429,93 | Oil | NMR(CDCl$_3$)δppm=7.45,s(4 aromatic protons: para-Cl phenyl); from 6.60 to 7.60,m(4 protons:2 aromatic and —CH=CH—);4.33,t(O—C$\underline{H}_2$); 3.78,s and 3.90,s(2OC$\underline{H}_3$);2.90,m (—CH$_2$—N piperidine);1.70, m(—N piperidine) I.R: —CO—CH=CH— bands at 1650 and 1630 cm$^{-1}$ |
| 26 | —N(piperidine) | 4-F | 2 | 2,3-dimethoxyphenoxy | $C_{24}H_{28}FNO_4$ | 413,47 | Oil | NMR(CDCl$_3$)δppm=6.5 to 7.6, m(6 aromatic H and C$\underline{H}$=C$\underline{H}$); 4.05,t(OC$\underline{H}_2$);3.65 and 3.78,s (2CH$_3$O);2.55,t(C$\underline{H}_2$—N)2.35 and 1.4,m(—N piperidine) |
| 27 | —N(piperidine) | 4-CH$_3$ | 2 | 2,3-dimethoxyphenoxy | $C_{25}H_{31}NO_4$ | 410,51 | Oil | NMR(CDCl$_3$)δppm=6.5 to 7.5, m(6 aromatic H and CH=CH); 4.1,t(OC$\underline{H}_2$);3.7 and 3.82,s (2C$\underline{H}_3$O);2.6,t(C$\underline{H}_2$—N)2.38 and 1.5,m(—N piperidine) |
| 28 | —N(piperidine) | 4-OCH$_3$ | 2 | 2,3-dimethoxyphenoxy | $C_{25}H_{31}NO_5$ | 425,51 | Oil | NMR(CDCl$_3$)δppm=6.5 to 7.6, m(6 aromatic H and CH=CH); 4.1,t(OC$\underline{H}_2$);3.7,3.78 and 3.82,s (3C$\underline{H}_3$O);2.6,t(C$\underline{H}_2$—N);2.4 and 1.4,m(N piperidine) |

TABLE II-continued (II) and (IIa)

| Code No. | $-N\begin{matrix}R_1\\R_2\end{matrix}$ | $(R)_n$ | m | $Ar\begin{matrix}\diagup\\O-\end{matrix}$ | Empirical formula | Molecular weight | Melting point (°C.) | ELEMENTARY ANALYSIS NMR SPECTRUM I.R. SPECTRUM |
|---|---|---|---|---|---|---|---|---|
| 29 | 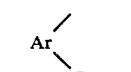 chlorhydrate + 4% H₂O | 2-OH | 2 | 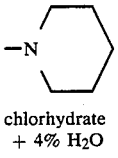 | $C_{24}H_{34}ClNO_5$ + 4% H₂O | 470,81 | 88 | %   C   H   N<br>Cal. 61,22 7,73 2,98<br>Obt. 61,50 7,93 2,97 |
| 30 | 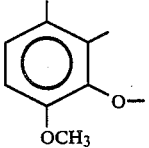 | 3-OH | 2 |  | $C_{24}H_{29}NO_5$ | 411,48 | Oil | NMR(CDCl₃)δppm=7.45,s(O$\underline{H}$); 6.5 to 7.4,m(6 aromatic H and C$\underline{H}$=C$\underline{H}$);4.1,t(OC$\underline{H}_2$);3.65 and 3.8,s(2C$\underline{H}_3$O);2.7,t(C$\underline{H}_2$—N);2.5 and 1.5,m(N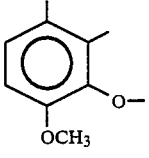) |
| 31 |  | 4-OH | 2 |  | $C_{24}H_{29}NO_5$ | 411,48 | 93 | NMR(CDCl₃)δppm=6.5 to 7.4, m(6 aromatic protons and —C$\underline{H}$=C$\underline{H}$—);4.20,t(—OC$\underline{H}_2$); 3.72 and 3.82,s(2—OC$\underline{H}_3$);2.6 and 1.55,m(—C$\underline{H}_2$—N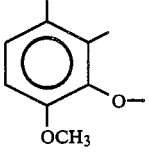) |
| 32 |  | 4-OH | 3 |  | $C_{25}H_{31}NO_5$ | 425,51 | | NMR(CDCl₃)δppm=6.6 to 7.6, m(O$\underline{H}$,6 aromatic H and C$\underline{H}$=C$\underline{H}$);4.1,t(OC$\underline{H}_2$);3.7 and 3.9,s(2C$\underline{H}_3$O);3;m (C$\underline{H}_2$—N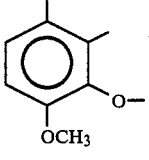);2,m(C$\underline{H}_2$ and N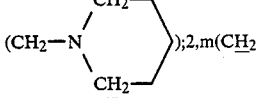) |
| 33 | 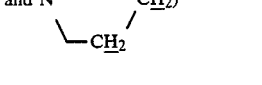 | 4-OH | 2 | 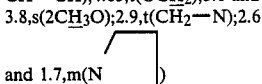 | $C_{23}H_{27}NO_5$ | 397,45 | 93 | NMR(CDCl₃)δppm=6.4 to 7.2, m(O$\underline{H}$,6 aromatic H and C$\underline{H}$=C$\underline{H}$);4.05,t(OC$\underline{H}_2$);3.6 and 3.8,s(2C$\underline{H}_3$O);2.9,t(C$\underline{H}_2$—N);2.6 and 1.7,m(N) |
| 34 | 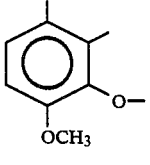 | 4-OH | 2 | 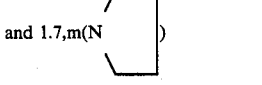 | $C_{23}H_{29}NO_5$ | 399,47 | 93 | NMR(CDCl₃)δppm=9.3,s(O$\underline{H}$); 6.5 to 7.4,m(6 aromatic H and C$\underline{H}$=C$\underline{H}$);4.1,t(OC$\underline{H}_2$);3.7 and 3.82,s(2C$\underline{H}_3$O);2.95,t(C$\underline{H}_2$—N); 2.65,q and 1.0,t(N) |

TABLE II-continued (II) and (IIa)

Structure: Ar–CO–CH=CH–C₆H₄(R)ₙ ; Ar–O–(CH₂)ₘ–NR₁R₂

| Code No. | –N(R₁)(R₂) | (R)ₙ | m | Ar / O– | Empirical formula | Molecular weight | Melting point (°C.) | ELEMENTARY ANALYSIS / NMR SPECTRUM / I.R. SPECTRUM |
|---|---|---|---|---|---|---|---|---|
| 35 | morpholino | 4-OH | 2 | 2,3-dimethoxyphenoxy (OCH₃ at 2 and 3 positions) | $C_{23}H_{27}NO_6$ | 413,45 | Oil | NMR(CDCl₃)δppm=6.6 to 7.4, m(O$\underline{H}$,6 aromatic H and CH=CH);4.1,t(OC$\underline{H_2}$);3.7 and 3.85,s(2C$\underline{H_3}$O);3.75,M and 2.6,m (C$\underline{H_2}$—N morpholino) |
| 36 (chlorhydrate) | piperidino | 4-OH | 2 | 2,3,5-trimethoxyphenoxy | $C_{25}H_{32}ClNO_6$ | 477,97 | 214 | % C H N<br>Cal. 62,82 6,75 2,93<br>Obt. 62,92 6,94 2,92 |
| 37 (chlorhydrate) | piperidino | 4-OH | 2 | 3,4,5-trimethoxyphenoxy | $C_{25}H_{32}ClNO_6$ | 477,97 | 235 | % C H N<br>Cal. 62,82 6,75 2,93<br>Obt. 60,45 6,66 2,97 |
| 38 | piperidino | 4-OH | 2 | 2-methoxyphenoxy | $C_{23}H_{27}NO_4$ | 381,45 | — | NMR(CDCl₃)δppm=6.4 to 7.4, m(O$\underline{H}$,7 aromatic H and CH=CH);4.1,t(OC$\underline{H_2}$);3.78,s (C$\underline{H_3}$O);2.88,t(C$\underline{H_2}$—N);2.5 and 1.4,m(—N piperidino) |
| 39 | piperidino | 4-OH | 2 | 2,5-dimethoxyphenoxy (OCH₃, CH₃O positions) | $C_{24}H_{29}NO_5$ | 411,48 | Oil | NMR(CDCl₃)δppm=6.4 to 7.4, m(4 aromatic H and CH=CH);6.2,s(O$\underline{H}$);6.12,s(2 aromatic H in 3 and 5);4.1,t (OC$\underline{H_2}$);3.7 and 3.8,s(2C$\underline{H_3}$O); 2.7,t(C$\underline{H_2}$—N);2.5m and 1.4,m (—N piperidino) |
| 40 | –N(CH₃)(CH₃) | 4-OH | 2 | 2,3-dimethoxyphenoxy | $C_{21}H_{25}NO_5$ | 371,42 | 163 | NMR(CDCl₃)δppm=6.5 to 7.6, m(O$\underline{H}$,6 aromatic H and CH=CH);4.08,t(OC$\underline{H_2}$);3.65 and 3.8,s(2OC$\underline{H_3}$);2.7,t(C$\underline{H_2}$—N(CH₃)₂); 2.30,s(—N(CH₃)₂) |

TABLE II-continued

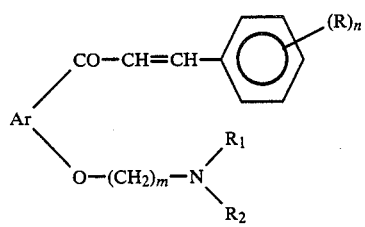
(II) and (IIa)

| Code No. | -N(R1)(R2) | (R)n | m | Ar-O- | Empirical formula | Molecular weight | Melting point (°C.) | ELEMENTARY ANALYSIS NMR SPECTRUM I.R. SPECTRUM |
|---|---|---|---|---|---|---|---|---|
| 41 | -N(Et)(Et) | 4-OH | 2 | (2,4,5-triOCH3-phenyl)-O- | $C_{24}H_{31}NO_6$ | 429,50 | 143 | NMR(CDCl3)δppm=6.6 to 7.4, m(OH,4 aromatic H and CH=CH);6.3,s(aromatic H in 5); 4.1,t(OCH2);3.7,3.8 and 3.9,s (3CH3O);2.9,t(CH2—N(Et)(Et));2.62q and 1.0,t(N(Et)(Et)) |
| 42 | -N(Et)(Et) | 4-OH | 2 | (2-OCH3-phenyl)-O- | $C_{23}H_{27}NO_4$ | 365,45 | Oil | NMR(CDCl3)δppm=6.7 to 7.5, m(OH and 7 aromatic H and CH=CH);4.2,t(OCH2);3.82,s (OCH3);2.9,t(CH2—N);2.62,q (N(CH2)(CH2));1.1,t(2CH3) |
| 43 | -N(piperidino) | 4-OCH2φ | 2 | (2,4,5-triOCH3-phenyl)-O- | $C_{31}H_{35}NO_5$ | 501,60 | 130 | % C H N<br>Cal. 74,22 7,03 2,79<br>Obt. 73,74 7,14 2,85 |
| 44 | -N(piperidino) | 3,4-di-OCH2φ | 2 | (2,6-diOCH3-phenyl)-O- | $C_{38}H_{42}NO_6$ | 607,72 | Oil | NMR(CDCl3)δppm=6.5 to 7.4 (15 aromatic H and CH=CH); 5.08 and 5.1,s(2CH2φ);4.1,t (OCH2);3.65 and 3.78,s(2OCH3); 2.6,t(CH2—N);2.4 and 1.5,m (—N(piperidino)) |

TABLE II'

| Code No. | Ar—O— | (R)ₙ | m | $\begin{array}{c}R_1\\ \diagdown\\ N\\ \diagup\\ R_2\end{array}$ | Form | Empirical formula | Molecular weight | Melting point (°C.) | ELEMENTARY ANALYSIS OR NMR SPECTRUM |
|---|---|---|---|---|---|---|---|---|---|
| 100 | 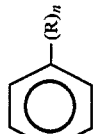 | OCH₂φ | 2 | 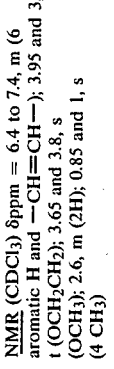 piperidine | Base | C₃₁H₃₄ClNO₅ | 536.05 | Oil | NMR (CDCl₃) δppm = 7.3, s(5 benzylic H); 6.6 to 7.5,m (5 aromatic H and CH=CH); 5, s (CH₂); 4.15 and 2.8, t (OCH₂—CH₂—); 3.6 and 3.85, s (OCH₃); 1.6 and 2.4, m (10 piperidinic H) |
| 101 |  | OH | 2 |  diisopropylamine | Base | C₂₅H₃₃NO₅ | 427.52 | Oil | NMR (CDCl₃) δppm = 6.4 to 7.4, m (6 aromatic H and —CH=CH—); 3.95 and 3, t (OCH₂CH₂); 3.65 and 3.8, s (OCH₃); 2.6, m (2H); 0.85 and 1, s (4 CH₃) |
| 102 | 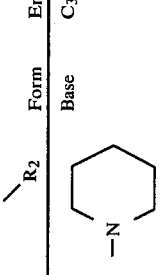 | 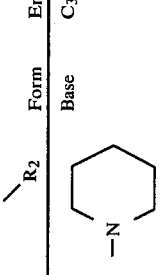 OCH₂φ | 2 |  cyclopentyl-NH | Base | C₃₁H₃₅NO₅ | 501.60 | Oil | NMR (CDCl₃) δppm = 7.35, s (5 benzylic H); 6.6 to 7.5, m (6 aromatic H and CH=CH); 5.05, s (CH₂); 4.2 and 2.8, t (OCH₂CH₂); 3.65 and 3.82, s (OCH₃); 3.5, m (NH); 1 to 2, m (9 H) |
| 103 | 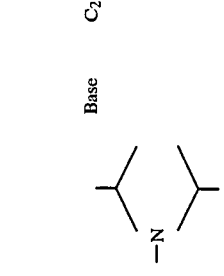 | 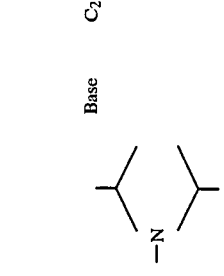 OCH₂φ | 2 | Et—N—Et | Base | C₃₂H₃₉NO₅ | 517.64 | Oil | NMR (CDCl₃) δppm = 7.35, s (5 benzylic H); 6.4 to 7.4, m (6 aromatic H and CH=CH); 5, s (OCH₂); 3.6 to 4.2, m (3 OCH₂); 2.3 to 2.9, m (3 CH₂); 0.8 to 1.5, m (4 CH₃) |

TABLE II'-continued (II) or (IIa)

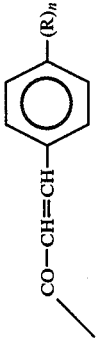

| Code No. | Ar—O— | (R)$_n$ | m | $\begin{array}{c} R_1 \\ -N \\ R_2 \end{array}$ | Form | Empirical formula | Molecular weight | Melting point (°C.) | ELEMENTARY ANALYSIS OR NMR SPECTRUM |
|---|---|---|---|---|---|---|---|---|---|
| 104 | 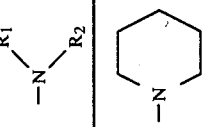 | OH | 2 | 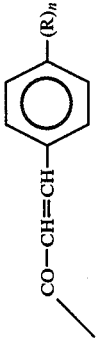 piperidine | Base | C$_{26}$H$_{31}$NO$_7$ | 469.52 | Oil | NMR (CDCl$_3$) δppm = 10, s (OH); 6.5 to 7.7, m (4 aromatic H and CH=CH); 4.38, s (—OCH$_2$CH$_2$O—); 4.20 and 2.8 t (OCH$_2$—CH$_2$); 3.75 and 3.85, s (OCH$_3$); 1.6 and 2.4, m (10 piperidinic H) |
| 105 | 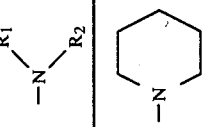 | OH | 2 | 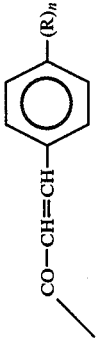 piperidine | Base | C$_{26}$H$_{33}$NO$_7$ | 471.53 | Oil | NMR (CDCl$_2$) δppm = 7.9, s (OH); 6.4 to 7.2, m (4 aromatic H and —CH=CH—); 4.10 and 2.65, t (OCH$_2$CH$_2$); 3.9, 3.82 and 3.70, s (4 OCH$_3$); 1.6 and 2.4, m (10 piperidinic H) |
| 106 | 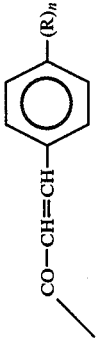 | OCH$_2$φ | 2 | 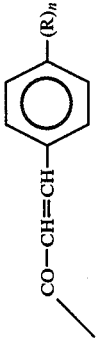 piperidine | Base | C$_{35}$H$_{37}$NO$_5$ | 551.65 | Oil | NMR (CDCl$_3$) δppm = 7.3, s (5 benzylic H); 8.1, m and 6.7 to 7.6, m (6 aromatic H and —CH=CH—); 5, s (OCH$_2$); 4.22 and 2.65, t (OCH$_2$CH$_2$); 3.85 and 3.98, s (OCH$_3$); 1.6 and 2.4, m (10 piperidinic H) |
| 107 | 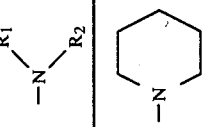 | OH | 2 | $\begin{array}{c} Et \\ -N \\ Et \end{array}$ | Base | C$_{23}$H$_{28}$ClNO$_5$ | 433.92 | <60 | NMR (CDCl$_3$) δppm = 6.4 to 7.4, m (5 aromatic H and —CH=CH—); 4.2 and 2.8, t (OCH$_2$CH$_2$); 3.65 and 3.8, s (OCH$_3$); 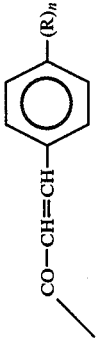; 0.98, t (2 CH$_3$). 2.5, t (N) |

TABLE II'-continued $$\text{Ar} - \text{O} - \overset{\displaystyle \text{CO}-\text{CH}=\text{CH}}{\underset{\displaystyle}{\bigcirc}} - \text{O}-(\text{CH}_2)_m - \text{N}\overset{R_1}{\underset{R_2}{}}$$

(R)_n (II) or (IIa)

| Code No. | Ar—O— | (R)_n | m | $\text{N}\overset{R_1}{\underset{R_2}{}}$ | Form | Empirical formula | Molecular weight | Melting point (°C.) | ELEMENTARY ANALYSIS OR NMR SPECTRUM |
|---|---|---|---|---|---|---|---|---|---|
| 108 | OCH₃ / OCH₃ / OCH₃ / Cl | OH | 2 | diisopropylamino | Base HCl | C₂₅H₃₂ClNO₅ C₂₅H₃₃Cl₂NO₅ | 461.97 498.44 | <60 234 | NMR (Base) CDCl₃ δppm = 6.28, s (OH); 6.6 to 7.4, m (5 aromatic H and —CH=CH—); 4.0 and 2.95, t (OCH₂CH₂); 3.7 to 3.8, s (OCH₃); 2.7, m (2H); 0.8 and 0.98, s (4 CH₃) |
| 109 | OCH₃ / OCH₃ / OCH₃ / F | OCH₂φ | 2 | piperidino | Base | C₃₁H₃₄FNO₅ | 519.59 | Oil | NMR (CDCl₃) δppm = 7.4, s (5 benzylic H); 6.5, d (aromatic H in α of fluor); 6.6 to 7.5, m (4 aromatic H and CH=CH); 5.1, s (OCH₂); 4.15 and 2.6, t (OCH₂CH₂); 3.65 and 3.85, s (OCH₃); 1.5, and 2.4, m (10 piperidinic H) |
| 110 | OCH₃ / OCH₃ / OCH₃ / Cl | OH | 2 | piperidino | Base | C₂₄H₂₈ClNO₅ | 445.93 | <50 | NMR (CDCl₃) δppm = 6.5 to 7.4, m (5 aromatic H and CH=CH); 4.4, s (OH); 4.15 and 2.6, t (OCH₂—CH₂); 3.7 and 3.8, s (OCH₃); 1.5 and 2.5, m (10 piperidinic H) |
| 111 | OCH₃ / OCH₃ / OCH₃ / O₂N | OH | 2 | piperidino | Base | C₂₄H₂₈N₂O₇ | 456.48 | Oil | NMR (CDCl₃) δppm = 6.5 to 7.6, m (5 aromatic H and CH=CH); 5.9, s (OH); 4.2 and 2.65, t (OCH₂CH₂); 3.78 and 3.9, s (OCH₃); 1.5 and 2.5, m (10 piperidinic H) |

TABLE II'-continued (II) or (IIa)

Ar—O—CO—CH=CH—(Ar)—(R)$_n$

O—(CH$_2$)$_m$—N(R$_1$)(R$_2$)

| Code No. | Ar—O— | (R)$_n$ | m | —N(R$_1$)(R$_2$) | Form | Empirical formula | Molecular weight | Melting point (°C.) | ELEMENTARY ANALYSIS OR NMR SPECTRUM |
|---|---|---|---|---|---|---|---|---|---|
| 112 | OCH$_3$, OCH$_3$, O$_2$N-phenyl | 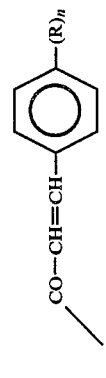 | 2 | piperidine (—N) | Base | C$_{29}$H$_{36}$N$_2$O$_8$ | 540.59 | Oil | |
| 113 | Cl, OCH$_3$, Cl-phenyl | OH | 2 | piperidine (—N) | Base | C$_{22}$H$_{23}$Cl$_2$NO$_3$ | 420.33 | <50 | NMR (CDCl$_3$) δppm = 6.5 to 7.4, m (6 aromatic H, —CH=CH— and OH); 4.2 and 2.75, t (OCH$_2$—CH$_2$); 1.5 and 2.5, m (10 piperidinic H) |
| 114 | OCH$_3$, Cl-phenyl | OH | 2 | piperidine (—N) | Base | C$_{22}$H$_{24}$ClNO$_3$ | 385.88 | 152 | NMR (CDCl$_3$) δppm = 6.7 to 7.7, m (7 aromatic H and —CH=CH—); 4.2 and 2.7, t (OCH$_2$CH$_2$); 1.4 and 2.4, m (10 piperidinic H) |
| 115 | OCH$_3$, OCH$_3$, Cl-phenyl | H | 2 | piperidine (—N) | Base | C$_{24}$H$_{28}$ClNO$_4$ | 429.93 | Oil | NMR (CDCl$_3$) δppm = 6.8 and 7.35, d (CH=CH); 7.4, m (6 aromatic H); 4.15 and 2.6, t (OCH$_2$CH$_2$); 3.7 and 3.85, s (OCH$_3$); 1.4 and 2.4, m (10 piperidinic H) |

TABLE II'-continued (II) or (IIa)

| Code No. | Ar—O— | (R)$_n$ | m | $\begin{array}{c}R_1\\|\\-N\\|\\R_2\end{array}$ | Form | Empirical formula | Molecular weight | Melting point (°C.) | ELEMENTARY ANALYSIS OR NMR SPECTRUM |
|---|---|---|---|---|---|---|---|---|---|
| 116 | 2,6-dimethoxy-3,4-dichloro-phenoxy | OH | 2 | piperidino | Base | C$_{24}$H$_{27}$Cl$_2$NO$_2$ | 480.38 | Past | NMR (CDCl$_3$) δppm = 6.4 to 7.2, m (4 aromatic H and CH=CH); 4.2, t and 2.7, t (OCH$_2$CH$_2$); 3.7 and 3.9, s (2 OCH$_3$); 2.5 and 1.5, m (10 piperidinic H) |
| 117 | 2,3-dimethyl-6-methoxyphenoxy | OH | 2 | piperidino | Base | C$_{24}$H$_{29}$NO$_4$ | 411.48 | <50 | NMR (CDCl$_3$) δppm = 6.4 to 7.2, m (6 aromatic H and CH=CH); 4, t and 2.7, t (O—CH$_2$—CH$_2$); 3.7, s (OCH$_3$); 2.25, s (CH$_3$); 2.5 and 1.5, m (10 piperidinic H) |
| 118 | 2-methyl-3-methoxy-4-chlorophenoxy | OH | 2 | piperidino | Base | C$_{23}$H$_{26}$ClNO$_4$ | 415.90 | 95 | NMR (CDCl$_3$); 8.1, s (OH); 6.5 to 7.4, m (6 aromatic H and CH=CH); 4.2 and 2.8, t (OCH$_2$—CH$_2$); 3.7 s (OCH$_3$); 1.5 and 2.5, m (10 piperidinic H) |

TABLE III $$\text{Ar}\begin{array}{c}\text{COR}_5\\|\\\end{array}\text{O—(CH}_2)_m\text{—N}\begin{array}{c}\text{R}_1\\\text{R}_2\end{array} \quad \text{(III) or (V)}$$

| Code No. | -N(R$_1$)(R$_2$) | m | Ar—O— | R$_5$ | Empirical formula | Molecular weight | Melting point (°C.) | ELEMENTARY ANALYSIS OR NMR SPECTRUM % C / H / N |
|---|---|---|---|---|---|---|---|---|
| 45 | piperidine | 2 | 2,3,4-trimethoxy-6-methylphenoxy | CH$_3$ | C$_{19}$H$_{27}$NO$_8$ | 397.41 | 155 | Cal. 57.42 / 6.85 / 3.52 ; 56.45 / 6.32 / 3.53 |
| 46 | piperidine | 3 | 2,3,4-trimethoxy-6-methylphenoxy | CH$_3$ | C$_{18}$H$_{27}$NO$_4$ | 321.40 | Oil | NMR(CDCl$_3$) δppm = 6.5, d and 6.9, d (J=9 Hz) (2 aromatic H in 4 and 5); 4.05, t (—O—CH$_2$); 3.75 and 3.85, s (2 CH$_3$O); 2.5, s (CH$_3$CO); 2.4, m (C$\underline{H}_2$N⟨piperidine⟩); 1.6, m (4CH$_2$) |
| 47 | pyrrolidine | 2 | 2,3,4-trimethoxy-6-methylphenoxy | CH$_3$ | C$_{16}$H$_{23}$NO$_4$ | 293.35 | Oil | NMR(CDCl$_3$) δppm = 6.55 and 6.9, d (J=9 Hz) (2 aromatic H in 4 and 5); 4.08, t (OC$\underline{H}_2$); 3.78 and 3.85, s (2 CH$_3$O); 2.9, t (C$\underline{H}_2$—N⟨pyrrolidine⟩); 2.5 s (CH$_3$CO); 2.6, m (N(C$\underline{H}_2$)$_2$); 1.9, m |

TABLE III-continued (III) or (V)

Structure: Ar—O—(CH₂)ₘ—N(R₁)(R₂), with COR₅ on Ar

| Code No. | -N(R₁)(R₂) | m | Ar—O— | R₅ | Empirical formula | Molecular weight | Melting point (°C.) | ELEMENTARY ANALYSIS OR NMR SPECTRUM |
|---|---|---|---|---|---|---|---|---|
| 48 | -N(Et)(Et) | 2 | 2,4-dimethoxy-3-methylphenyl (OCH₃, CH₃, OCH₃) | CH₃ | C₁₆H₂₅NO₄ | 295.37 | Oil | NMR(CDCl₃) δppm = 6.6 and 6.9, d (J=9 Hz) (2 aromatic H in 4 and 5); 4.10, t (O—CH₂); 3.75 and 3.82, s (2 CH₃O); 2.9, t (CH₂—N); 2.65, q (N—CH₂); 2.5, s (CH₃CO); 1.05, t (2 CH₃) |
| 49 | morpholino | 2 | 2,4-dimethoxy-3-methylphenyl | CH₃ | C₁₆H₂₃NO₅ | 309.21 | Oil | NMR(CDCl₃) δppm = 6.55 and 6.9, d (J=9 Hz) (2 aromatic H in 4 and 5); 4.10, t (OCH₂); 3.78 and 3.8, s (2 CH₃O); 3.7, m (N—CH₂—CH₂—O morpholino); 2.7, t (CH₂—N morpholino); 2.6, m; 2.5, s (CH₃CO) |
| 50 | piperidino | 2 | 3,5-dimethoxy-2-methylphenyl | CH₃ | C₁₇H₂₅NO₄ | 307.38 | Oil | NMR(CDCl₃) δppm = 6.10, s (2 aromatic H); 4.1, t (—OCH₂); 3.76 and 3.80, s (2 OCH₃); 2.45, s (—COCH₃); 2.7, t (CH₂—N); 2.4 and 1.5, m (N piperidino) |
| 51 | -N(Et)(Et) | 2 | 2,3-dimethoxy-5-methylphenyl | CH₃ | C₁₆H₂₃NO₃ | 277.35 | Oil | NMR(CDCl₃) δppm = 6.9 to 7.2, m (3 aromatic H); 4.12, t (OCH₂); 3.85, s (OCH₃); 2.8, t (CH₂—N); 2.63, s (CH₃CO); 1.0, t (2 CH₃); 2.6, q (N(CH₂)₂) |

TABLE III-continued (III) or (V)

$$Ar\begin{array}{c}COR_5\\O-(CH_2)_m-N\end{array}\begin{array}{c}R_1\\R_2\end{array}$$

| Code No. | $\begin{array}{c}R_1\\-N\\R_2\end{array}$ | m | Ar—O— | $R_5$ | Empirical formula | Molecular weight | Melting point (°C.) | ELEMENTARY ANALYSIS OR NMR SPECTRUM % C H N |
|---|---|---|---|---|---|---|---|---|
| 52 | piperidine (—N with 5-membered ring shown) | 2 | 2,3-dimethoxyphenyl with OCH₃ groups | CH₃ | $C_{16}H_{23}NO_3$ | 277.35 | Oil | NMR(CDCl₃) δppm = 7.28, t (aromatic H in 4); 6.6, d (2 aromatic H in 3 and 5); 4.12, t (CH₂O); 3.82, s (CH₃O); 2.72, t (—CH₂—N piperidine); 2.5, s (CH₃CO). |
| 53 | $\begin{array}{c}CH_3\\-N\\CH_3\end{array}$ | 2 | 2,4,6-trimethoxyphenyl (OCH₃, OCH₃, OCH₃) | CH₃ | $C_{14}H_{21}NO_4$ | 267.32 | Oil | NMR(CDCl₃) δppm = 6.58 and 6.9, d (2 aromatic H in 4 and 5); 4.12, t (OCH₂); 3.75 and 3.82, s (2 CH₂O); 2.65, t (CH₂—N); 2.5, s (CH₃CO); 2.32, s (N(CH₃)(CH₃)). |
| 54 | $\begin{array}{c}Et\\-N\\Et\end{array}$ | 2 | 3,4,5-trimethoxyphenyl with CH₃O and OCH₃ groups | CH₃ | $C_{17}H_{27}NO_5$ | 325.39 | Oil | NMR(CDCl₃) δppm = 6.3, s (aromatic H in 5); 4.18, t (OCH₂); 3.78, 3.80 and 3.9, s (3 CH₃O); 2.9, t (CH₂—N); 2.6, q (N(CH₂CH₃)(CH₂CH₃)); 1.05, t (CH₃). |

TABLE III $$\text{Ar} \begin{matrix} \text{COR}_5 \\ | \\ \text{O(CH}_2)_m\text{—N} \end{matrix} \begin{matrix} R_1 \\ \\ R_2 \end{matrix}$$

(III) and (V)

| Code No. | Ar—O— | —R₅ | m | —N\<R₁R₂ | Form | Empirical Formula | Molecular weight | Melting point (°C.) | ELEMENTARY ANALYSIS OR NMR SPECTRUM |
|---|---|---|---|---|---|---|---|---|---|
| 130 | 3,5-(OCH₃)₂, 2-CH₃, 6-Cl phenoxy | —CH₃ | 2 | piperidino | Base | C₁₇H₂₄ClNO₄ | 341.83 | Oil | NMR (CDCl₃) δ ppm = 6.65, s (1 aromatic H); 4.2 and 2.65, t (OCH₂—CH₂); 3.78 and 3.9, s (OCH₃); 2.5, s (COCH₃); 1.5 and 2.4, m (10³ piperidinic H) |
| 131 | 3,5-(OCH₃)₂, 2-CH₃ phenoxy | —CH₃ | 2 | diisopropylamino | Base | C₁₈H₂₉NO₄ | 323.42 | Oil | NMR (CDCl₃) δ ppm = 6.45 and 6.75, d (2 aromatic H); 3.85 and 2.7, t (OCH₂CH₂); 3.7 and 3.78, s (OCH₃); 2.8, m (2H in α of nitrogen); 0.9 and 1.0, s (4CH₃); 2.4, s (COCH₃) |
| 132 | 3,5-(OCH₃)₂, 2-CH₃ phenoxy | —CH₃ | 2 | cyclopentylamino | Base | C₁₇H₂₅NO₄ | 307.38 | Oil | NMR (CDCl₃) δ ppm = 7.4, s (NH); 6.5 and 6.85, d (2 aromatic H); 4.15 and 2.85, t (OCH₂CH₂—); 2.45, s (COCH₃); 2.1, m and 1.4 to 2.1, m (9 pyrrolidinic H) |
| 133 | 3,5-(OEt)₂, 2-CH₃ phenoxy | —CH₃ | 2 | diethylamino | Base | C₁₈H₂₉NO₄ | 323.42 | Oil | NMR (CDCl₃) δ ppm = 6.5 and 6.8, d (2 aromatic H); 3.8 to 4.2, m (3OCH₂); 2.5, s (COCH₃); 2.4 to 2.95, m (3CH₂ in α of nitrogen); 0.9 to 1.6, m (4CH₃) |

TABLE III-continued $$\underset{Ar}{\overset{COR_5}{\diagdown}}O(CH_2)_m-N\underset{R_2}{\overset{R_1}{\diagdown}} \quad \text{(III) and (V)}$$

| Code No. | Ar—O— | —R$_5$ | m | $-N\diagup^{R_1}_{R_2}$ | Form | Empirical Formula | Molecular weight | Melting point (°C.) | ELEMENTARY ANALYSIS OR NMR SPECTRUM |
|---|---|---|---|---|---|---|---|---|---|
| 134 | 2,3-dimethoxy-5,6-(ethylenedioxy)phenyl with OCH$_3$ groups | —CH$_3$ | 2 | piperidine | Base | C$_{19}$H$_{27}$NO$_6$ | 365.41 | Oil | NMR (CDCl$_3$) δ ppm = 4.25, s (O—CH$_2$CH$_2$O); 4.05 and 2.7, t (O—CH$_2$—CH$_2$—N); 3.75 and 3.82, s (OCH$_3$); 2.45, s (COCH$_3$); 1.5 and 2.4, m (10 piperidinic H) |
| 135 | tetramethoxyphenyl | —CH$_3$ | 2 | piperidine | Base | C$_{19}$H$_{29}$NO$_6$ | 367.43 | Oil | NMR (CDCl$_3$) δ ppm = 4.1 and 2.65, t (OCH$_2$CH$_2$); 3.82, 3.9 and 3.95, s (4OCH$_3$); 2.55, s (COCH$_3$); 1.5 and 2.5, m (10 piperidinic H). |
| 136 | dimethoxynaphthyl | —CH$_3$ | 2 | piperidine | Base | C$_{21}$H$_{25}$NO$_4$ | 355.42 | Oil | NMR (CDCl$_3$) δ ppm = 7.4 and 8.0, m (4 aromatic H); 4.3 and 2.7, t (OCH$_2$CH$_2$); 3.9 and 4.0, s (OCH$_3$); 2.6, s (COCH$_3$); 1.6 and 2.5, m (10 piperidinic H) |
| 137 | chlorodimethoxyphenyl with OCH$_3$ | —CH$_3$ | 2 | $-N\diagup^{Et}_{Et}$ | Base | C$_{16}$H$_{24}$ClNO$_4$ | 329.82 | Oil | NMR (CDCl$_3$) δ ppm = 6.6, s (1 aromatic H); 4.1 and 2.7, t (OCH$_2$CH$_2$); 3.75 and 3.82, s (OCH$_3$); 2.45, s (COCH$_3$); 2.5 and 1, t (N$\diagup^{Et}_{Et}$). |

TABLE III-continued $$\underset{Ar}{\overset{COR_5}{\diagdown}}\underset{O(CH_2)_m-N}{\overset{}{\diagdown}}\underset{R_2}{\overset{R_1}{\diagdown}} \quad\text{(III) and (V)}$$

| Code No. | Ar—O— | —R$_5$ | m | —N(R$_1$)(R$_2$) | Form | Empirical Formula | Molecular weight | Melting point (°C) | ELEMENTARY ANALYSIS OR NMR SPECTRUM |
|---|---|---|---|---|---|---|---|---|---|
| 138 | 4-Cl, 2,3,5-tri-OCH$_3$-phenoxy | —CH$_3$ | 2 | 2,6-diisopropylpiperidino | Base | C$_{18}$H$_{28}$ClNO$_4$ | 357.87 | Oil | NMR (CDCl$_3$) δ ppm = 6.6, s (1 aromatic H); 3.95 and 2.7, t (OCH$_2$CH$_2$); 3.75 and 3.82, s (OCH$_3$); 2.45, s (COCH$_3$); 3, m and 0.9 and 1.1, s |
| 139 | 4-F, 2,3,5-tri-OCH$_3$-phenoxy | —CH$_3$ | 2 | piperidino | Base | C$_{17}$H$_{24}$FNO$_4$ | 325.37 | Oil | NMR (CDCl$_3$) δ ppm = 6.45, d (1 aromatic H); 4.15 and 2.65, t (OCH$_2$CH$_2$); 2.45, s (COCH$_3$); 1.5 and 2.4, m (10 piperidinic H); 3.7 and 3.8, s (OCH$_3$) |
| 140 | 4-Cl, 2,3,5-tri-OCH$_3$-phenoxy | —CH$_3$ | 2 | piperidino | Base | C$_{17}$H$_{24}$ClNO$_4$ | 341.83 | Oil | NMR (CDCl$_3$) δ ppm = 6.9, s (1 aromatic H); 4.1 and 2.6, t (OCH$_2$CH$_2$); 3.8 and 3.85, s (OCH$_3$); 2.5, s (COCH$_3$); 1.5 and 2.5, m (10 piperidinic H) |
| 141 | 4-NO$_2$, 2,3,5-tri-OCH$_3$-phenoxy | —CH$_3$ | 2 | piperidino | Base | C$_{17}$H$_{24}$N$_2$O$_6$ | 352.38 | Oil | NMR (CDCl$_3$) δ ppm = 7.5, s (1 aromatic H); 4.25 and 2.6, t (OCH$_2$CH$_2$); 3.8 and 3.85, s (OCH$_3$); 2.5, (COCH$_3$); 1.5 and 2.4, m (10 piperidinic H) |

TABLE III-continued $$\text{Ar} \diagdown O(CH_2)_m \diagdown N \diagup R_1 \diagdown R_2 \quad \text{(III) and (V)}$$

(with COR₅ on Ar)

| Code No. | Ar—O— | —R₅ | m | —N(R₁)(R₂) | Form | Empirical Formula | Molecular weight | Melting point (°C.) | ELEMENTARY ANALYSIS OR NMR SPECTRUM |
|---|---|---|---|---|---|---|---|---|---|
| 142 | 2,6-dichloro-methoxyphenoxy | —CH₃ | 2 | piperidino | Base | C₁₅H₁₉Cl₂NO₂ | 316.22 | Oil | NMR (CDCl₃) δ ppm = 7.05 and 7.3, d (2 aromatic H); 4.1 and 2.65, t (OCH₂CH₂); 1.5 and 2.4, m (10 piperidinic H); 2.55, s (COCH₃) |
| 143 | 4-chloro-2-methoxyphenoxy | —CH₃ | 2 | piperidino | Base | C₁₅H₂₀ClNO₂ | 281.77 | Oil | NMR (CDCl₃) δ ppm = 7.6, d and 6.9, m (3 aromatic H); 4.1 and 2.7, t (OCH₂CH₂); 2.6, s (COCH₃); 1.4 and 2.4, m (10 piperidinic H) |
| 144 | 2-methoxyphenoxy | —CH(CH₃)₂ | 2 | piperidino | Base | C₁₇H₂₅NO₂ | 275.38 | Oil | NMR (CDCl₃) δ ppm = 6.9 and 7.4, m (4 aromatic H); 4.2 and 2.7, t (OCH₂CH₂); 3.55, m and 1.05 and 1.2, s (CH(CH₃)₂); 1.5 and 2.4, m (10 piperdinic H) |
| 145 | 3,5-dichloro-2,6-dimethoxy-4-methoxyphenoxy | —CH₃ | 2 | piperidino | Base | C₁₇H₂₃Cl₂NO₄ | 376.28 | Oil | NMR (CDCl₃) δ ppm = 4.2 and 2.6, t (OCH₂CH₂); 3.78 and 3.9, s (2OCH₃); 2.5, s (COCH₃); 1.4 and 2.4, m (10 piperidinic H) |

TABLE III-continued $$\text{Ar} \diagdown \begin{matrix} COR_5 \\ O(CH_2)_m-N \diagdown \begin{matrix} R_1 \\ R_2 \end{matrix} \end{matrix} \quad \text{(III) and (V)}$$

| Code No. | Ar—O— | —R$_5$ | m | —N$\diagdown^{R_1}_{R_2}$ | Form | Empirical Formula | Molecular weight | Melting point (°C.) | ELEMENTARY ANALYSIS OR NMR SPECTRUM |
|---|---|---|---|---|---|---|---|---|---|
| 146 | OCH$_3$, CH$_3$, OCH$_3$, Cl substituted phenoxy | —CH(CH$_3$)$_2$ | 2 | piperidino | Base | C$_{19}$H$_{28}$ClNO$_4$ | 369.88 | Oil | NMR (CDCl$_3$) δ ppm = 6.65, s (1 aromatic H); 4.2 and 2.6, t (OCH$_2$CH$_2$); 3, m, 1.05 and 1.2, s CH$_3$ (CH$\diagdown^{}_{CH_3}$); 1.6 and 2.5, m (10 piperdinic H) |
| 147 | OCH$_3$, CH$_3$ substituted phenoxy | —CH$_3$ | 2 | piperidino | Base | C$_{17}$H$_{25}$NO$_3$ | 291.38 | Oil | NMR (CDCl$_3$) δ ppm = 6.55 and 7.1, d (2 aromatic H); 3.9 and 2.65, t (OCH$_2$CH$_2$); 3.78, s (OCH$_3$); 2.5, s (COCH$_3$); 2.2, s (CH$_3$); 1.5 and 2.4, m (10 piperdinic H) |
| 148 | OCH$_3$, Cl substituted phenoxy | —CH$_3$ | 2 | piperidino | Base | C$_{16}$H$_{22}$ClNO$_2$ | 311.80 | Oil | NMR (CDCl$_3$) δ ppm = 6.6 and 7.3 d (2 aromatic H); 4.1 and 2.65, t (OCH$_2$CH$_2$); 3.75, s (OCH$_3$); 2.5, s (COCH$_3$); 1.5 and 2.5, m (10 piperidinic H) |

The derivatives of formula (I) and their pharmaceutically acceptable salts have been tested on laboratory animals and have shown pharmacological activities and particularly an activity antagonistic to calcium.

These activities have been more especially demonstrated by the test of depolarization of the dog isolated coronary arteries, carried out in accordance with the following procedure.

Dogs, of both sexes, from 12 to 25 kg are anaesthetized with sodic pentobarbital (30 mg/kg/i.v.) and the intraventricular branch of the left coronary artery is removed. Fragments are cut off from the proximal portion (1.5 cm in length and $\geq 2$ mm in diameter) and distal portion (0.5 to 1 cm in length and $\leq 0.5$ mm in diameter) and are kept in a Tyrode bath at 37° C. equilibrated by a constant flow of a mixture of oxygen (95%) and carbon dioxid gas (5%). They are connected to an isotonic myograph under a tension of 1.5 g for the fragment coming from the proximal portion (proximal fragment) and 0.2 g for the fragment from the distal portion (distal fragment),. An hour after obtaining equilibrium, the survival medium is replaced by a hyperpotassic medium (35 m M/l) and the smooth muscles contract. The addition of derivatives of formula (I) or of the salts thereof then causes relaxation of these muscles.

Some results obtained with the derivatives of formula (I) and their pharmaceutically acceptable salts in the above test are given as examples in Table IV herebelow which further shows the acute toxicity of the tested compounds and which is estimated on mice according to the method of MILLER and TAINTER (Proc. Soc. Exp. Biol. Med. (1944), 57, 261).

TABLE IV

| Code Number | LD$_{50}$ Mice (mg/kg/i.v.) | Dose of tested derivative causing 50% reduction of the contraction induced by the hyperpotassic medium [IC 50 (Moles)] | |
|---|---|---|---|
| | | Proximal fragment | Distal fragment |
| 2 | 14 | $6.4 \cdot 10^{-6}$ | $1.3 \cdot 10^{-6}$ |
| 5 | 33 | $1.6 \cdot 10^{-6}$ | $5.4 \cdot 10^{-7}$ |
| 10 | 20 | $2.1 \cdot 10^{-7}$ | $1.9 \cdot 10^{-7}$ |
| 12 | 23 | $9 \cdot 10^{-8}$ | $1 \cdot 10^{-7}$ |
| 14 | 33 | $2.9 \cdot 10^{-7}$ | $2.4 \cdot 10^{-7}$ |
| 3 | 16 | $5.5 \cdot 10^{-7}$ | $1.1 \cdot 10^{-6}$ |
| 4 | 31 | $2.7 \cdot 10^{-7}$ | $1.6 \cdot 10^{-6}$ |
| 6 | 31 | $8.9 \cdot 10^{-7}$ | $4.4 \cdot 10^{-7}$ |
| 7 | 27 | $2.9 \cdot 10^{-6}$ | $2.1 \cdot 10^{-6}$ |
| 8 | 12 | $9.1 \cdot 10^{-7}$ | $7.3 \cdot 10^{-7}$ |
| 9 | 11 | $4.1 \cdot 10^{-7}$ | $6.4 \cdot 10^{-7}$ |
| 11 | 22 | $3.3 \cdot 10^{-6}$ | $1.7 \cdot 10^{-6}$ |
| 13 | 27 | $4.2 \cdot 10^{-7}$ | $4.8 \cdot 10^{-7}$ |
| 60 | 8.9 | $1 \cdot 10^{-6}$ | $1 \cdot 10^{-6}$ |
| 61 | — | $2.4 \cdot 10^{-6}$ | — |
| 62 | 13 | $4.3 \cdot 10^{-7}$ | — |
| 66 | 15.7 | $1 \cdot 10^{-6}$ | — |
| 67 | 32.5 | $4.5 \cdot 10^{-6}$ | — |
| 68 | 12.3 | $2.9 \cdot 10^{-7}$ | — |
| 69 | 8.6 | $1.3 \cdot 10^{-8}$ | — |
| 70 | 14 | $3.2 \cdot 10^{-8}$ | — |
| 71 | 11.5 | $8.3 \cdot 10^{-8}$ | — |
| 72 | 3.4 | $1.4 \cdot 10^{-8}$ | — |
| 73 | 11.7 | $5.1 \cdot 10^{-8}$ | — |
| 74 | 18.6 | $4.1 \cdot 10^{-8}$ | — |
| 75 | — | $9.9 \cdot 10^{-7}$ | — |
| 76 | — | $1.5 \cdot 10^{-5}$ | — |
| 77 | 43 | $1.8 \cdot 10^{-6}$ | — |

The difference between toxic doses and active doses permits the use in therapeutics of the derivatives of formula (I) and the pharmaceutically acceptable salts thereof, among others for the treatment of affections related to a disturbance of the intra and extra cellular movements of calcium and particularly troubles of the cardiovascular system, particularly as antiangorous, antirhythmic, antihypertension agents and vasodilators.

The present invention also relates to the pharmaceutical compositions containing at least one derivative of formula (I) or one of their pharmaceutically acceptable salts, in combination with a pharmaceutically acceptable vehicle.

These compositions will be administered orally in the form of tablets, pills or capsules containing up to 500 mg of active ingredient (1 to 5 per day) and in the form of drops dosed to 10% (20 drops, 3 times per day), rectally in the form of suppositories containing up to 300 mg of active ingredient (1 to 2 per day) or else in the form of injectable ampoules containing up to 300 mg of active ingredient (1 to 2 per day).

We claim:

1. Aminoalkoxy aromatic derivative, corresponding to the formula:

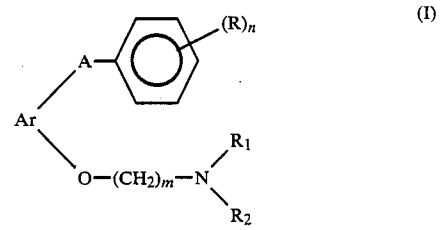

in which:

R represents a hydrogen or halogen atom, a methyl, hydroxyl or alkoxy group in which the alkyl residue contains 1 to 4 carbon atoms, or a benzyloxy group;

n takes the value 1 when R=H or 2 when R is different from H;

m takes the value 2 or 3;

A represents a chain having any one of the following structures:

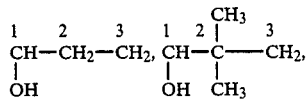

the aromatic group Ar being linked to position 1 of this chain;

the pair (R$_1$,R$_2$) is (M, C$_1$-C$_4$alkyl), (M, C$_5$-C$_6$cycloalkyl), (M, cycloalkylalkyl containing from 4 to 8 carbon atoms) or (C$_1$-C$_4$alkyl, C$_1$-C$_4$alkyl) when A is

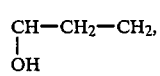

and is (C$_1$-C$_4$alkyl, C$_1$-C$_4$alkyl) when A is

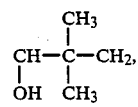

and

Ar represents:

either a benzene group of structure:

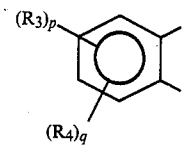

in which $R_3$ represents a halogen atom or a nitro or methyl group, $R_4$=alkoxy with 1 to 4 carbon atoms, p=0, 1 or 2; q=1, 2, 3, 4; p+q≦4;

or a naphthalene or benzodioxannic group respectively of structure:

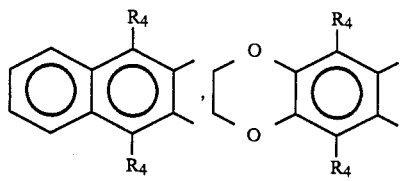

where $R_4$ has the same meanings as previously, as well as its mineral or organic acid addition salts.

2. The derivative and salt as claimed in claim 1, wherein A represents the chain

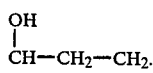

3. The derivative and salt as claimed in claim 2, wherein m=2.

4. The derivative and salt as claimed in claim 3, wherein the set

$(R)_n$, $NR_1R_2$) takes any one of the following values:

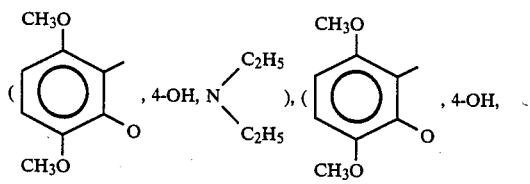

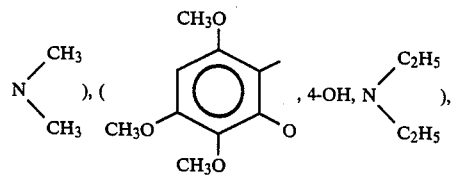

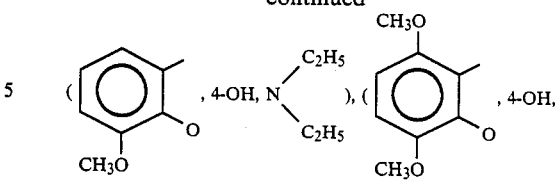

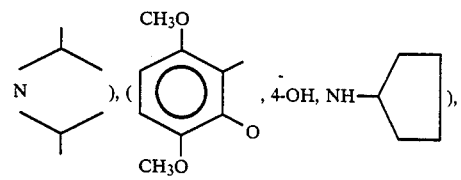

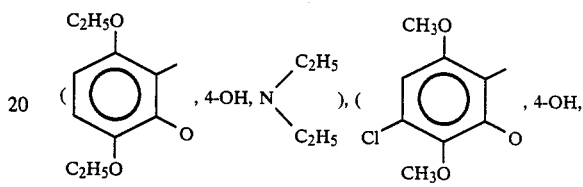

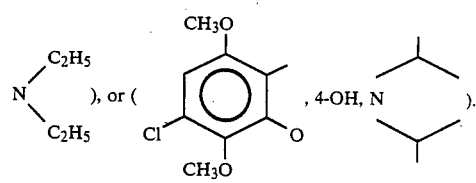

5. The derivative and salt as claimed in claim 3, wherein the set

$(R)_n$, $NR_1R_2$) takes any one of the following values:

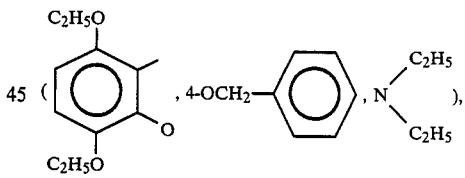

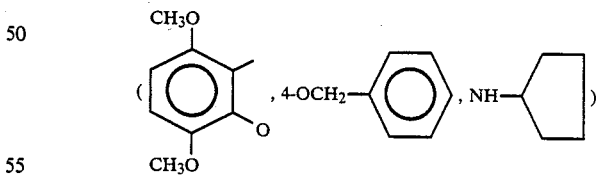

6. A pharmaceutical composition having an activity antagonistic to calcium comprising a therapeutically effective amount of a compound as claimed in claim 1, in combination with a pharmaceutically acceptable carrier.

* * * * *